US011708571B2

(12) United States Patent
Krebs et al.

(10) Patent No.: US 11,708,571 B2
(45) Date of Patent: Jul. 25, 2023

(54) PRODUCTION OF 2-KETO-3-DEOXY-D-GLUCONIC ACID IN FILAMENTOUS FUNGI

(71) Applicant: BP CORPORATION NORTH AMERICA INC., Houston, TX (US)

(72) Inventors: Molly Krebs, Naperville, IL (US); Chris Phillips, Naperville, IL (US); Fernando Valle, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 17/056,146

(22) PCT Filed: May 14, 2019

(86) PCT No.: PCT/US2019/032232
§ 371 (c)(1),
(2) Date: Nov. 17, 2020

(87) PCT Pub. No.: WO2019/222226
PCT Pub. Date: Nov. 21, 2019

(65) Prior Publication Data
US 2021/0214706 A1 Jul. 15, 2021

Related U.S. Application Data

(60) Provisional application No. 62/672,719, filed on May 17, 2018.

(51) Int. Cl.
*C12N 9/88* (2006.01)
*C12P 7/42* (2006.01)
*C12N 1/14* (2006.01)

(52) U.S. Cl.
CPC .............. *C12N 9/88* (2013.01); *C12N 1/14* (2013.01); *C12P 7/42* (2013.01); *C12Y 401/02014* (2013.01)

(58) Field of Classification Search
CPC .............. C12N 9/88; C12N 1/14; C12P 7/42
See application file for complete search history.

(56) References Cited

U.S. PATENT DOCUMENTS

2015/0118730 A1* 4/2015 Ju .................... C12N 9/248
435/272

FOREIGN PATENT DOCUMENTS

| WO | 00/37667 A1 | 6/2000 |
| WO | 2016/141148 A1 | 9/2016 |
| WO | 2019/222226 A2 | 11/2019 |

OTHER PUBLICATIONS 4.1.2.1. UniProt Database. Retrieved on-line on Jun. 14, 2022.*
EC 4.1.2.51. BRENDA Database. Retrieved on-line on Jun. 14, 2022.*
International Search Report for International Application No. PCT/US2019/032232, dated Dec. 20, 2019.
(Continued)

*Primary Examiner* — Yong D Pak
(74) *Attorney, Agent, or Firm* — Biospark Intellectual Property Law

(57) ABSTRACT

A recombinant filamentous fungi that includes reduced 2-Keto-3-Deoxy-Gluconate (KDG) aldolase enzyme activity as compared to the filamentous fungi not transformed to have reduced KDG aldolase enzyme activity is provided. Also provided is a method of producing KDG.

15 Claims, 4 Drawing Sheets

Specification includes a Sequence Listing.

(56) References Cited

OTHER PUBLICATIONS

Written Opinion of the International Searching Authority for International Application No. PCT/US2019/032232, dated Dec. 20, 2019.
Elshafei et al., 1989 "Formation of 2-keto-3-deoxy aldonic acids by cell-free extracts of Aspergillus ustus." Enzyme and Microbial Technology. 11(6): 367-369.
Database Embl [Online], "Aspergillus niger contig An16c0230, genomic contig." Accessed Jan. 2007.

* cited by examiner

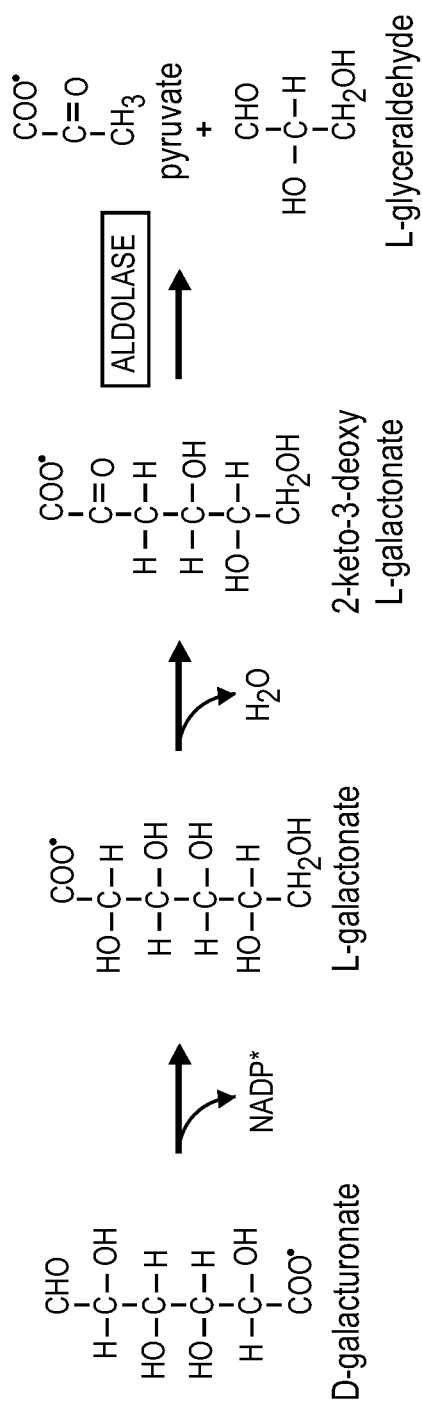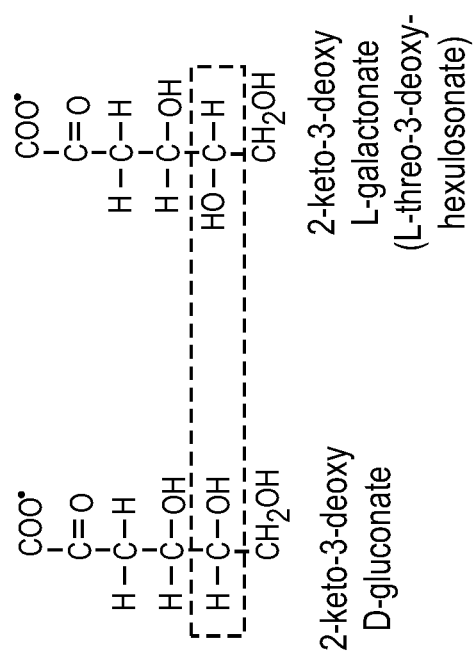
FIGURE 4A
FIGURE 4B

PRODUCTION OF 2-KETO-3-DEOXY-D-GLUCONIC ACID IN FILAMENTOUS FUNGI

CROSS-REFERENCE TO RELATED APPLICATIONS

This application claims benefit of priority under 35 U.S.C. § 119(e) of U.S. Ser. No. 62/672,719, filed May 17, 2018, the entire contents of which is incorporated herein by reference in its entirety.

INCORPORATION OF SEQUENCE LISTING

The material in the accompanying sequence listing is hereby incorporated by reference into this application. The accompanying sequence listing text file, name BP17000_1WO_Sequence_Listing, was created on May 14, 2019, and is 18 kb. The file can be accessed using Microsoft Word on a computer that uses Windows OS.

FIELD OF THE INVENTION

The present invention relates generally to transformed filamentous fungi and more specifically to methods for producing 2-Keto-3-Deoxy-Gluconate (KDG).

BACKGROUND OF THE INVENTION

The use of keto sugar intermediates to produce furan derivatives such as Furan Dicarboxylic Acid (FDCA), offers an important alternative to the use of 5-hydroxymethylfurfural (HMF) that is obtained from fructose. One of the advantages of certain sugar keto-intermediates is that they have a higher propensity than fructose to acquire a furanose conformation, which is advantageous for further catalytic steps that lead to FDCA or other furan-derivatives. The percentage of furanose conformation that several keto sugar-derivatives have in solution has been previously described (WO 2016/141148). Among them, 2-Keto-3-Deoxy-D-Gluconic acid (KDG) is an interesting intermediate because it forms a furanose ring more efficiently than fructose; and because it can be produced from gluconate by a single enzymatic step using a gluconate dehydratase (Matsubara et al. (2014)). Furthermore, as shown in FIG. 1 and FIG. 2, KDG is a normal intermediate during gluconate catabolism in microorganisms that use the non-phosphorylative Entner-Doudoroff pathway (Conway, T. (1992)); from hexuronates catabolism (Suvorova et al. (2011)); or from degradation of pectin and alginates (Hobbs J K. (2016)).

SUMMARY OF THE INVENTION

The present invention is based on the discovery that filamentous fungi can be used for producing 2-Keto-3-Deoxy-D-Gluconic acid (KDG) and other sugar acid derivatives via fermentation processes.

Accordingly, the present disclosure provides a genetically modified filamentous fungi that includes reduced 2-Keto-3-Deoxy-Gluconate (KDG) aldolase enzyme activity as compared to the wild type filamentous fungi.

In one embodiment, the filamentous fungi is an *Aspergillus* strain.

In another embodiment, the filamentous fungi is an *Aspergillus niger* strain.

In a further embodiment, the *Aspergillus niger* strain is NRRL 322, NRRL 328, NRRL 566, NRRL 599 or NRRL 2270.

In one embodiment, the genetic modification results in reduced endogenous KDG aldolase enzyme activity.

In an additional, the genetic modification is a mutation.

In certain embodiments, the mutation is a frame shift mutation, a substitution mutation, an insertion mutation, a loss of function mutation, a gain of function mutation, an inactivation mutation, a translocation mutation and/or a deletion mutation.

In a further embodiment, the mutation is in the promoter region, the 3' untranslated region, the 5' untranslated region and/or a regulatory sequence of a 2-Keto-3-Deoxy-Gluconate (KDG) aldolase gene.

In one embodiment, the mutation is in a nucleic acid sequence encoding a polypeptide having at least 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1.

In an additional embodiment, the mutation is a deletion of a gene having the nucleic acid sequence of SEQ ID NO:2.

In a further embodiment, the mutation is in a nucleic acid sequence encoding a KDG aldolase enzyme comprising the amino acid sequence of SEQ ID NO:1.

In another embodiment, the mutation inhibits the expression of the polypeptide comprising SEQ ID NO:1.

In a further embodiment, the enzyme having reduced 2-Keto-3-Deoxy-Gluconate (KDG) aldolase enzyme activity has the classification of EC4.1.2.51.

The disclosure also provides methods of producing 2-Keto-3-Deoxy-Gluconate (KDG). The methods include transforming a filamentous fungi with a nucleic acid sequence; and culturing the transformed filamentous fungi in a culture medium, wherein the level of KDG produced in the transformed filamentous fungi is higher than the level of KDG accumulated in the filamentous fungi not transformed with the nucleic acid sequence, thereby producing KDG.

In one embodiment, the nucleic acid sequence inactivates a gene encoding a KDG aldolase enzyme, reduces expression of a gene encoding a KDG aldolase enzyme or inhibits expression of a gene encoding a KDG aldolase enzyme. In one embodiment, the nucleic acid sequence integrates into the filamentous fungi genome, and or the nucleic acid sequence introduces a frame shift mutation, a substitution mutation, an insertion mutation, a loss of function mutation, a gain of function mutation, an inactivation mutation, a translocation mutation and a deletion mutation.

In another, embodiment, the filamentous fungi is an *Aspergillus* strain.

In an additional embodiment, the filamentous fungi is an *Aspergillus niger* strain. In another embodiment, the nucleic acid sequence of the gene encoding the KDG aldolase enzyme comprises at least 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:2.

In a further embodiment, the amino acid sequence of the KDG aldolase enzyme comprises at least 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1. In another embodiment, nucleic acid sequence comprises SEQ ID NO:8.

In a further embodiment, the *Aspergillus niger* strain is NRRL 322, NRRL 328, NRRL 566, NRRL 599 or NRRL 2270.

In an additional embodiment, KDG is converted to 5-hydroxymethylfuranoic acid (HMFA) and/or Dicarboxylic acid (FDCA).

The disclosure additionally provides a DNA construct that includes SEQ ID NO:8.

In one embodiment, the DNA construct comprises a heterologous nucleic acid sequence.

The disclosure further provides an expression vector for expressing 2-Keto-3-Deoxy-Gluconate (KDG) aldolase, wherein the expression vector includes a DNA sequence encoding a polypeptide having the amino acid sequence comprising SEQ ID NO:1.

In one embodiment, the expression vector expresses a polypeptide comprising SEQ ID NO:1.

The disclosure also provides an expression vector for expressing 2-Keto-3-Deoxy-Gluconate (KDG) aldolase, wherein the expression vector includes a DNA sequence substantially similar to SEQ ID NO:2.

The disclosure additionally provides a method of decreasing D-glyceraldehyde production from 2-Keto-3-Deoxy-Gluconate in a filamentous fungi. The method includes transforming a filamentous fungi with a nucleic acid sequence; and culturing the transformed filamentous fungi in a culture medium, wherein the level of D-glyceraldehyde production from 2-Keto-3-Deoxy-Gluconate, in the transformed filamentous fungi, is decreased from the level of glyceraldehyde production from 2-Keto-3-Deoxy-Gluconate in a filamentous fungi not transformed with the nucleic acid sequence, thereby decreasing D-glyceraldehyde from 2-Keto-3-Deoxy-Gluconate.

In one embodiment, the nucleic acid sequence inactivates a gene encoding a KDG aldolase enzyme, reduces expression of a gene encoding a KDG aldolase enzyme or inhibits expression of a gene encoding a KDG aldolase enzyme. In one embodiment, the nucleic acid sequence integrates into the filamentous fungi genome, and or the nucleic acid sequence introduces a frame shift mutation, a substitution mutation, an insertion mutation, a loss of function mutation, a gain of function mutation, an inactivation mutation, a translocation mutation and a deletion mutation.

In an additional embodiment, the filamentous fungi is an *Aspergillus* strain.

In another embodiment, the filamentous fungi is an *Aspergillus niger* strain.

In a further embodiment, the *Aspergillus niger* strain NRRL 322, NRRL 328, NRRL 566, NRRL 599 or NRRL 2270.

In certain embodiments, the nucleic acid sequence of the gene encoding the KDG aldolase enzyme comprises SEQ ID NO:2.

In another embodiment, the amino acid sequence of the KDG aldolase enzyme comprises at least 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1.

Other aspects and advantages of the invention will be apparent from the following description and the appended claims.

BRIEF DESCRIPTION OF THE DRAWINGS

FIGS. 4 A-B show (A) Proposed D-Galacturonate degradation pathway in filamentous fungi (Martens-Uzunova, E. and Shcaap, P J. 2008) and (B) Differences between 2-keto-3-deoxy-D-gluconate and 2-keto-3-deoxy-L-galactonate. The position of hydroxyl-group different on both molecules is indicated by the dotted box.

DETAILED DESCRIPTION OF THE INVENTION

Figure 1:
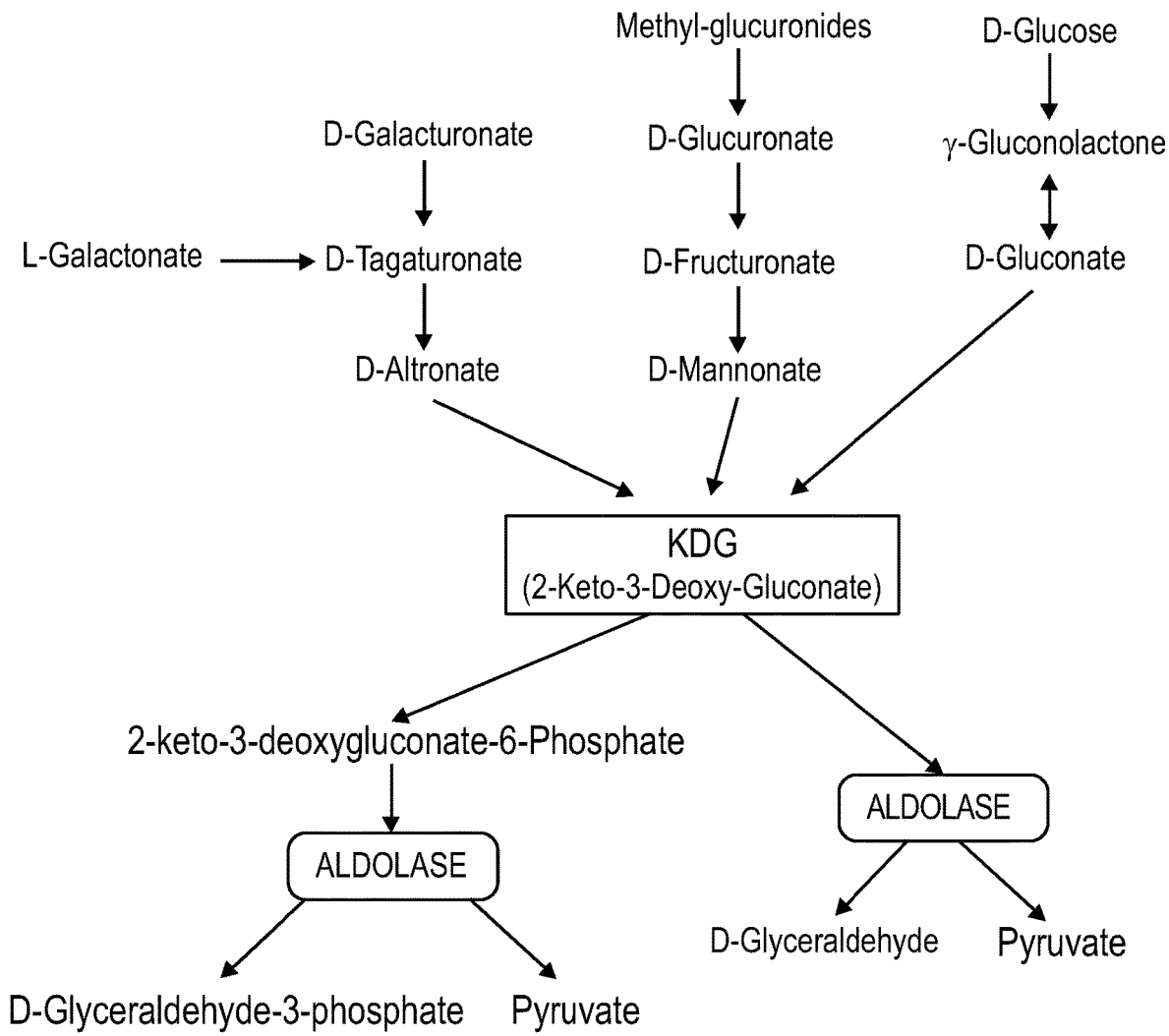
FIG. 1 shows a summary of the metabolic pathways that some microorganisms utilize to metabolize different sugars, and use KDG as an intermediate.
Figure 2:
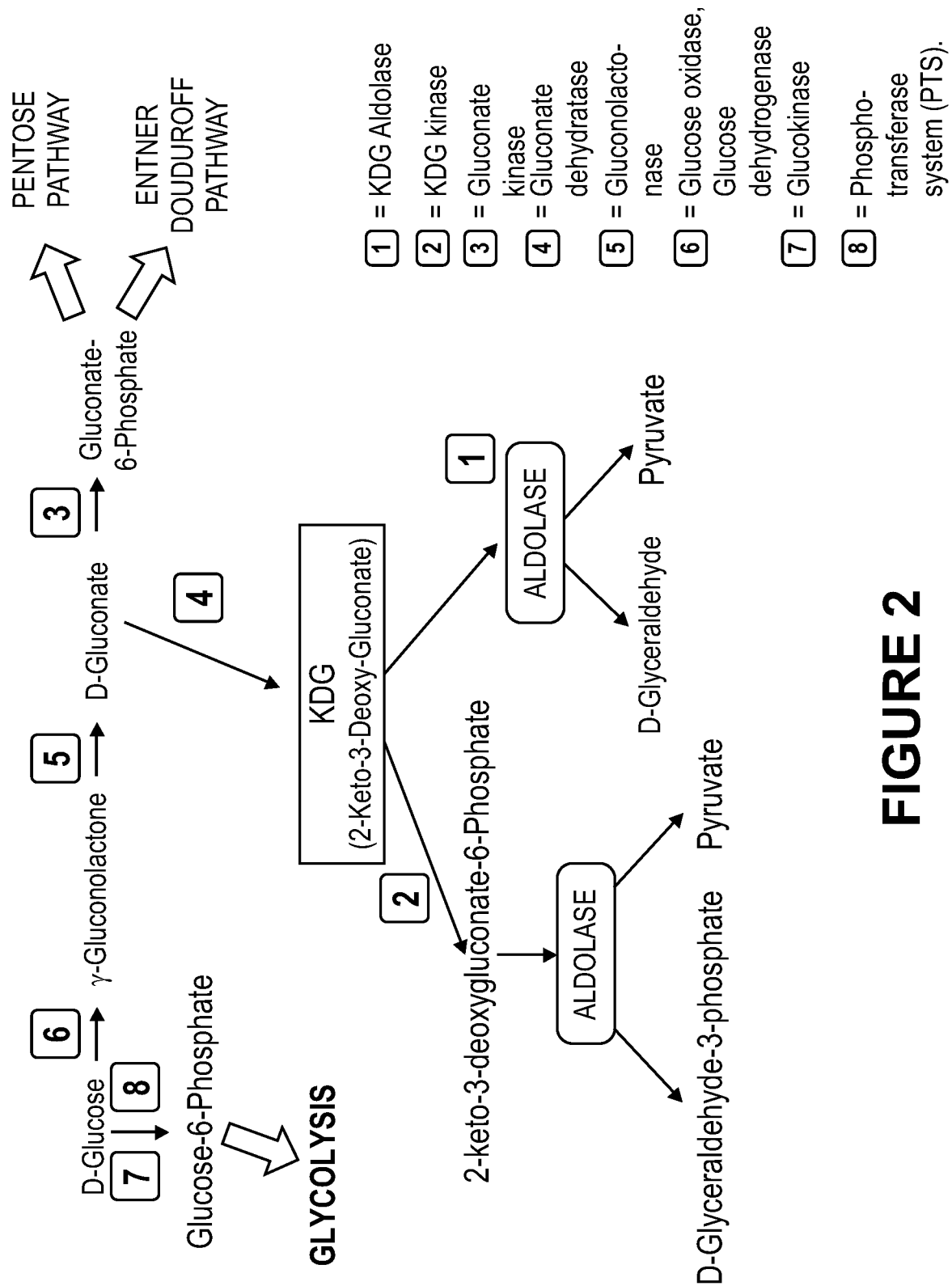
FIG. 2 shows a summary of the metabolic pathways and enzymes that some microorganisms utilize to metabolize Glucose and Gluconate, and use KDG as an intermediate.
Figure 3:
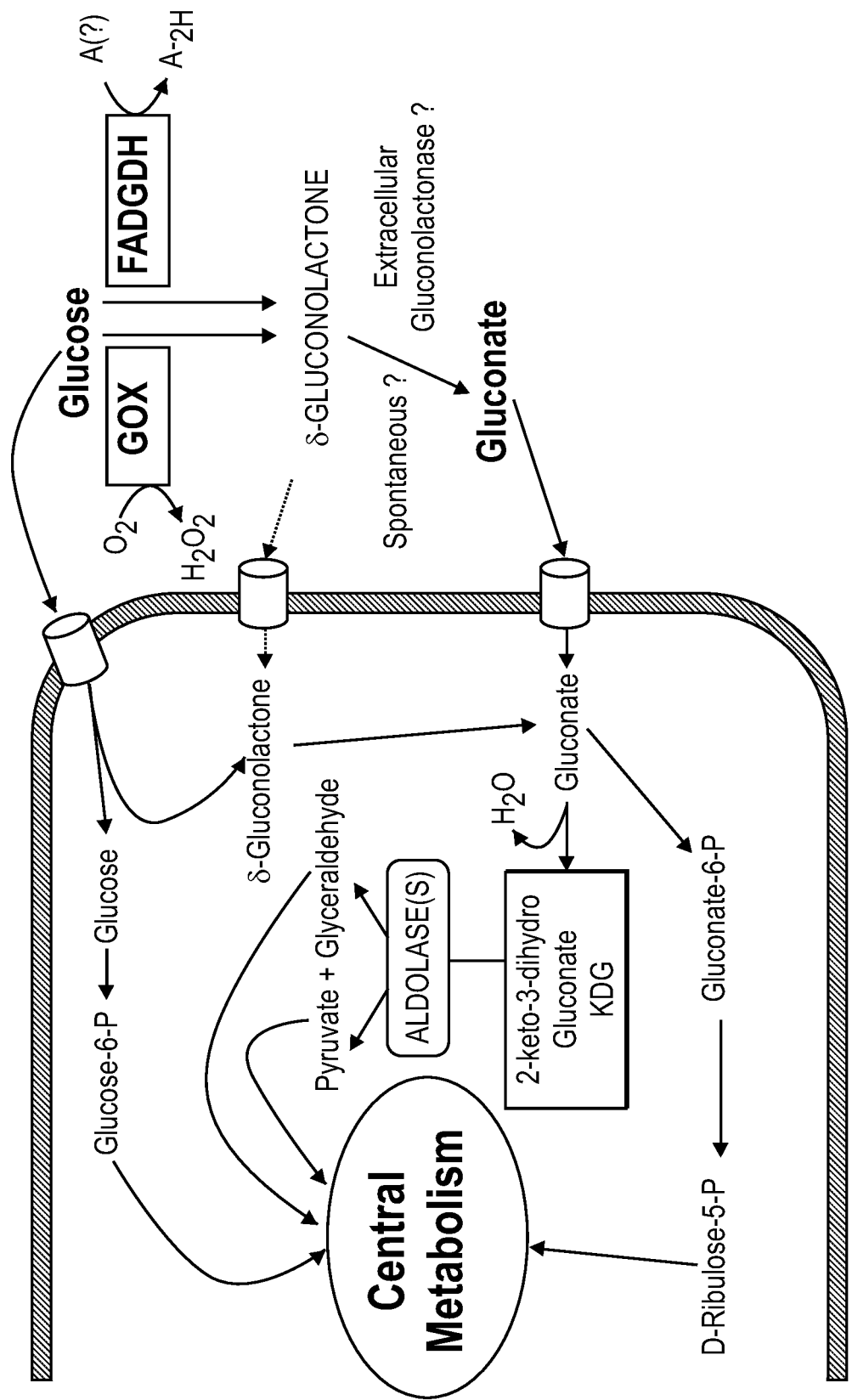
FIG. 3 shows Glucose and Gluconate assimilation in *Aspergillus niger* based on analysis of its genome (Flipphi et al. 2009) and the KDG pathway proposed by Elzainy et al. 1973. As reported for other microorganism (van Dijken et al. 2002), another possible pathway where γ-gluconolactone is transported into the cell first, and then converted into gluconate, is indicated by dotted arrows.

The present invention is based on the seminal discovery that filamentous fungi can be used for producing 2-Keto-3-Deoxy-D-Gluconic acid (KDG) and other sugar acid derivatives via fermentation processes.

Before the present methods and compositions are described, it is to be understood that this invention is not limited to particular methods, compositions, and experimental conditions described, as such methods, compositions, and conditions may vary. It is also to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" include one or more procedures/methods, and/or steps of the type described herein which will become apparent to those persons skilled in the art upon reading this disclosure and so forth.

With the goal of producing KDG and other sugar acids derivatives via fermentation processes, filamentous fungi like *Aspergillus* and *Trichoderma* strains are attractive production hosts, due to their wide use at the commercial level, for the production of enzymes and chemical compounds like gluconic, citric and itaconic acids. In this sense, gluconic acid-overproducing strains from *Aspergillus niger* were envisioned to be a good starting point to develop KDG and KDG-derivatives commercial processes, due to the fact that gluconate can be easily converted into KDG via gluconate-dehydratase enzymes. Furthermore, *Aspergillus. niger* may already be able to produce KDG as a normal intermediate during gluconate metabolism. However, there are conflicting reports on how *Aspergillus. niger* metabolizes gluconate: Müller, H M. (1984 and 1985) reported that certain *Aspergillus. niger* strains use the traditional pentose pathway by first phosphorylating gluconate to form gluconate-6-phosphate. In contrast, Elzainy et al. (1973) and Allam et al. (1975) have shown that other strains of *Aspergillus niger* catabolize D-gluconate by dehydrating it first to form KDG, which is subsequently cleaved by a KDG-aldolase, producing D-glyceraldehyde and pyruvate. These two products are further metabolized via the glycolytic pathway. More recently, the genome analysis of *Aspergillus niger* and other *Aspergillus* species, did not reveal any evidence for the presence of a KDG-forming pathway (Pel et al. 2007; Flipphi et al. 2009). Furthermore, these authors proposed several putative gluconokinases that could be responsible for converting gluconate into gluconate-6-phosphate for its assimilation via the normal pentose pathway.

Accordingly, the disclosure provides a genetically modified filamentous fungi that includes reduced 2-Keto-3-Deoxy-Gluconate (KDG) aldolase enzyme activity as compared to the wild type filamentous fungi.

Filamentous fungi are eukaryotic organisms that include *Aspergillus* and, specifically, *Aspergillus niger*. Specific examples of *Aspergillus niger* strains include NRRL 322, NRRL 328, NRRL 566, NRRL 599 or NRRL 2270.

The filamentous fungi of the present invention are genetically modified to reduce KDG-aldolase enzyme activity. One method of genetically modifying the fungi is by mutation wherein the organisms genome is altered such that KDG-aldolase enzyme activity is reduced. Mutations include a frame shift mutation, a substitution mutation, an insertion mutation, a loss of function mutation, a gain of function mutation, an inactivation mutation, a translocation mutation and/or a deletion mutation.

Mutations occur anywhere along the genome. Specifically, mutations may be in the promoter region, the 3' untranslated region, the 5' untranslated region and/or a regulatory sequence of a gene. A regulatory sequence is a segment of a nucleic acid molecule which is capable of increasing or decreasing the expression of specific genes within an organism.

In the present invention, the mutation can be in a nucleic acid sequence encoding a polypeptide having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1.

Additionally, the mutation can be a deletion of a gene having the nucleic acid sequence of SEQ ID NO:2. The mutation can also be in a nucleic acid sequence encoding a KDG aldolase enzyme comprising the amino acid sequence of SEQ ID NO:1. Additionally, the mutation can reduce or inhibit the expression of the polypeptide comprising SEQ ID NO:1.

Further, in the present invention, the enzyme having reduced 2-Keto-3-Deoxy-Gluconate (KDG) aldolase enzyme activity has the classification of EC4.1.2.51.

The disclosure also provides methods of producing 2-Keto-3-Deoxy-Gluconate (KDG). The method includes transforming a filamentous fungi with a nucleic acid sequence; and culturing the transformed filamentous fungi in a culture medium, wherein the level of KDG produced in the transformed filamentous fungi is higher than the level of KDG accumulated in the filamentous fungi not transformed with the nucleic acid sequence, thereby producing KDG.

In one embodiment, the nucleic acid sequence inactivates a gene encoding a KDG aldolase enzyme, reduces expression of a gene encoding a KDG aldolase enzyme or inhibits expression of a gene encoding a KDG aldolase enzyme. In one embodiment, the nucleic acid sequence integrates into the filamentous fungi genome, and or the nucleic acid sequence introduces a frame shift mutation, a substitution mutation, an insertion mutation, a loss of function mutation, a gain of function mutation, an inactivation mutation, a translocation mutation and a deletion mutation.

In one embodiment the insertion and integration of the nucleic acid into the filamentous fungi genome can inactivate a gene encoding a KDG aldolase enzyme or reduce or inhibit the expression of a gene encoding a KDG aldolase enzyme.

The filamentous fungi may be an *Aspergillus* strain and, specifically, an *Aspergillus niger* strain. Additionally, the *Aspergillus niger* strain can be NRRL 322, NRRL 328, NRRL 566, NRRL 599 or NRRL 2270.

In the present invention, the nucleic acid sequence of the gene encoding the KDG aldolase enzyme comprises at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:2.

Additionally, the amino acid sequence of the KDG aldolase enzyme comprises at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1.

In the present invention, the nucleic acid sequence that integrates into the filamentous fungi genome comprises SEQ ID NO:8.

The KDG that is produce can be further modified and converted into other furan derivatives. The KDG can be converted to 5-hydroxymethylfuranoic acid (HMFA) and/or Dicarboxylic acid (FDCA) through chemical methods known in the art.

The disclosure additionally provides a DNA construct that includes SEQ ID NO:8. In one embodiment, the DNA construct comprises a heterologous nucleic acid sequence. A heterologous nucleic acid sequence is a nucleic acid sequence derived from another organism or cell type.

The disclosure provides an expression vector for expressing 2-Keto-3-Deoxy-Gluconate (KDG) aldolase, wherein the expression vector includes a DNA sequence encoding a polypeptide having the amino acid sequence comprising SEQ ID NO:1. The expression vector can express a polypeptide comprising SEQ ID NO:1. The disclosure also provides an expression vector for expressing 2-Keto-3-Deoxy-Gluconate (KDG) aldolase, wherein the expression vector includes a DNA sequence substantially similar to SEQ ID NO:2

The invention provides methods of amplifying a nucleic acid encoding a polypeptide comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. Optionally, the promoter can be a fungal, yeast, viral, bacterial, mammalian, plant, synthetic or hybrid promoter. The promoter can be a constitutive promoter. In another aspect, the promoter can be an inducible promoter. In one aspect, the promoter can be a tissue-specific promoter or an environmentally regulated or a developmentally regulated promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cells comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods of editing of an organisms genome. One such method is the use of CRISPR. CRISPR-Cas9 is a unique technology that enables the editing parts of the genome by removing, adding or altering sections of the DNA sequence. Specifically, delivering the Cas9 nuclease complexed with a synthetic guide RNA (gRNA) into a cell enables the cell's genome can be cut at a desired location, allowing existing genes to be removed and/or new ones added.

The invention provides methods for modifying codons in a nucleic acid encoding a polypeptide; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid.

The invention provides methods of generating variants of the nucleic acids of the invention. These methods can be repeated or used in various combinations to generate polypeptides having an altered or different activity encoded by the template or wild type nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

In one aspect, the term "variant" refers to polynucleotides or polypeptides of the invention modified at one or more base pairs, codons, introns, exons, or amino acid residues (respectively) yet still retain the biological activity of a KDG of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), and any combination thereof.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The invention also provides methods for modifying the polypeptides of the invention by either natural processes, such as post-translational processing (e.g., phosphorylation, acylation, etc.), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd ed., W.H. Freeman and Company, New York (1993); Posttranslational Covalent Modification of Proteins, B. C. Johnson, Ed., Academic Press, New York, pp. 1-12 (1983). "Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related, e.g., only has conservative amino acids substitutions. Fragments which have different three dimensional structures as the naturally occurring protein are also included. An example of this is a "pro-form" molecule, such as a low activity proprotein, that can be modified by cleavage to produce a mature enzyme with significantly higher activity.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related, e.g., only has conservative amino acids substitutions. Fragments which have different three dimensional structures as the naturally occurring protein are also included. An example of this is a "pro-form" molecule, such as a low activity proprotein, that can be modified by cleavage to produce a mature enzyme with significantly higher activity.

The term "substantially similar" refers to nucleic acid or amino acid sequences having sequence variation that do not materially affect the nucleic acid or the amino acid sequence. With particular reference to nucleic acid sequences, the term "substantially similar" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially similar" refers generally to conservative substitutions and/or variations in regions of the polypeptide not involved in determination of structure or function.

The term "codon optimized" refers to a nucleic acid coding region that has been adapted for expression in the cells of a given host by replacing at least one, or more than one, or a significant number, of codons with one or more codons that are more frequently used in the genes of that host.

The disclosure additionally provides a method of decreasing D-glyceraldehyde production from 2-Keto-3-Deoxy-Gluconate in a filamentous fungi. The method includes transforming a filamentous fungi with a nucleic acid sequence; and culturing the transformed filamentous fungi in a culture medium, wherein the level of D-glyceraldehyde production from 2-Keto-3-Deoxy-Gluconate, in the transformed filamentous fungi, is decreased from the level of glyceraldehyde production from 2-Keto-3-Deoxy-Gluconate in a filamentous fungi not transformed with the nucleic acid sequence, thereby decreasing D-glyceraldehyde from 2-Keto-3-Deoxy-Gluconate.

In one embodiment, the nucleic acid sequence inactivates a gene encoding a KDG aldolase enzyme, reduces expression of a gene encoding a KDG aldolase enzyme or inhibits expression of a gene encoding a KDG aldolase enzyme. In one embodiment, the nucleic acid sequence integrates into the filamentous fungi genome, and or the nucleic acid sequence introduces a frame shift mutation, a substitution mutation, an insertion mutation, a loss of function mutation, a gain of function mutation, an inactivation mutation, a translocation mutation and a deletion mutation.

The insertion and integration of the nucleic acid into the filamentous fungi genome can inactivate a gene encoding a KDG aldolase enzyme or reduce or inhibit the expression of a gene encoding a KDG aldolase enzyme.

The filamentous fungi may be an *Aspergillus* strain and, specifically, an *Aspergillus niger* strain. Additionally, the *Aspergillus niger* strain can be NRRL 322, NRRL 328, NRRL 566, NRRL 599 or NRRL 2270.

The present invention provides, the nucleic acid sequence of the gene encoding the KDG aldolase enzyme comprises SEQ ID NO:2.

Additionally, the amino acid sequence of the KDG aldolase enzyme comprises at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:1.

The invention provides an isolated, synthetic or recombinant nucleic acid comprising a nucleic acid sequence having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to invention sequences. For example, such sequences include SEQ ID NO:2, SEQ ID NO:3 and SEQ ID NO:8. The invention further includes variants/modifications of the foregoing sequences.

Methods disclosed in the present invention and/or methods known to one of ordinary skill in the art may be used to isolate nucleic acids having a sequence with at least 99%, at least 98%, at least 97%, at least 95%, at least 90%, at least 80% or at least 70% homology to a nucleic acid sequence as set forth in SEQ ID NO:2, SEQ ID NO:3 and SEQ ID NO:8, sequences substantially identical thereto, or fragments comprising at least 10, 15, 20, 25, 30, 35, 40, 50, 75, 100, 150, 200, 300, 400, 500, 600, 700, 800, 900 or more consecutive bases thereof, and the sequences complementary to any of the foregoing sequences. Homology may be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to a nucleic acid sequence as set forth in SEQ ID NO:2, SEQ ID NO:3 and SEQ ID NO:8, or sequences complementary thereto.

Another aspect of the invention comprises polypeptides having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to invention sequences, e.g., SEQ ID NO:1. The invention further includes variants/modifications of the foregoing sequence discussed below.

Additionally, the methods disclosed in the present invention may be used to isolate nucleic acids which encode polypeptides having at least 99%, at least 95%, at least 90%, at least 85%, at least 80%, or at least 70% homology to a polypeptide having a sequence as set forth in SEQ ID NO:1, sequences substantially identical thereto, or fragments comprising at least 5, 10, 15, 20, 25, 30, 35, 40, 50, 75, 100, 150, 200, 250, 300 or more consecutive amino acids thereof as determined using a sequence alignment algorithm (e.g., such as the FASTA version 3.0t78 algorithm with the default parameters).

Another aspect of the invention is an isolated or purified polypeptide comprising a sequence as set forth in SEQ ID NO:1, sequences substantially identical thereto, or fragments comprising at least 5, 10, 15, 20, 25, 30, 35, 40, 50, 75, 100, 150, 200, 250, 300 or more consecutive amino acids thereof. As disclosed in the present invention and/or known to one of ordinary skill in the art, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

As discussed below, significant KDG aldolase enzymatic activity was measured in cell extracts from 5 different Aspergillus niger strains. Furthermore, after purifying this putative KDG-aldolase, the structural gene for such an enzyme was identified and inactivated, and it was demonstrated that an Aspergillus niger strain carrying this KDG-aldolase deletion was able to accumulate KDG. This indicates the importance of eliminating or attenuating the KDG-aldolase activity for KDG overproduction.

In sum, KDG aldolase activity was measured in 5 different Aspergillus niger strains.

An enzyme with KDG aldolase activity was purified from one of the strains; and based on LC-MS/MS based proteomic, protein G3Y6P2 from Aspergillus niger ATCC 1015 was identified (SEQ ID NO:1). This protein sequence was annotated as EHA21505 in GenBank, and is coded by ASPNIDRAFT_214527 (or Aspni5_214527). The protein sequence showed that it was a previously unknown enzyme, with unknown function, annotated in GenBank as Hypothetical protein or Dihydrodipicolinate synthase family protein. Compared with the 2-keto-3-deoxy-L-galactonate aldolase from Aspergillus niger, EHA21505 has 43% identity. As shown on Table 5, Blast searches indicated that this enzyme is well conserved in other Aspergillus niger close relatives.

Based on gene EHA21505 DNA sequence (SEQ ID: 2), a deletion cassette was constructed where the EHA21505 coding sequence was replaced by the Hygromycin B antibiotic resistance marker (SEQ ID: 8). This cassette was used to delete the gene in a lab strain described below.

Compared with the wild type strain, the Aspergillus niger strain containing the deletion of EHA21505 showed 7× less KDG-aldolase activity.

On solid media containing gluconate as the only carbon source, the KDG-aldolase deleted strain showed impaired growth.

In liquid cultures with gluconate as the only carbon source, the deleted strain accumulated a significant amount of KDG, while the wild type strain under the same conditions, did not accumulated any KDG.

An E. coli codon-optimized gene was synthesized and cloned in an expression vector. Cell-extracts from an E. coli strain carrying this plasmid showed KDG-aldolase activity.

In addition to the possible use of KDG to produce FDCA and other furan-derivatives, KDG could also be used in a similar application to gluconate and other sugar acids, for example: (1) as a chelating agent for detergents and beverages; (2) for anti-scaling applications; (3) as a de-icer; (4) as a corrosion-inhibitor; (5) as an additive to enhance metal and amine removal in refinery desalting processes, etc. Furthermore, because KDG and its dehydration derivatives will have at least 2 carbonyl groups, it may have better properties than gluconate and other sugar acids for current and future applications.

The following examples are provided to further illustrate the advantages and features of the present invention, but are not intended to limit the scope of the invention. While they are typical of those that might be used, other procedures, methodologies, or techniques known to those of skill in the art may alternatively be used.

EXAMPLES

Example 1

Growth of Aspergillus niger Strains and Preparation of Cell-Extracts

Aspergillus niger strains NRRL 322, NRRL 328, NRRL 566, NRRL 599, and NRRL 2270 (NRRL Culture Collection) were sporulated on Potato Dextrose Agarose plates and then spores from each strain were inoculated into 50 mL of potato dextrose broth in a 250 mL flask. The flasks were incubated in a shaker incubator at 30° C. at 150 rpm and grown for up to 72 hours. Mycelia were harvested by centrifugation, then resuspended in ~40 mL of Czapek Dox broth with sucrose excluded and 5% sodium gluconate as a the sole carbon source. The flasks were returned to the shaker incubator at 30° C. and 150 rpm and incubated for up to 48 hours. Cells were then lysed via sonication to generate cell lysates. Lysates were buffer exchanged into 200 mM sodium phosphate buffer pH 8.0 using gel filtration on PD-10 columns to reduce background absorbance.

Example 2

KDG Aldolase Assay of *Aspergillus niger* Lysates

Lysates were then tested using a lactate dehydrogenase coupled reaction to monitor NADH loss spectrophotometrically at 340 nm. The assay mixture was prepared with 0.2 mM NADH, 4 U/mL lactate dehydrogenase, 10 mM Na Phosphate pH 7.0, and an appropriate volume of lysate. The mixture was warmed to 30° C. and the reaction was initiated by addition of KDG-Li salt (Sigma p/n 12271) at 10 mM. Reactions were monitored in a cuvette and a reading was taken every 30 seconds for 2 minutes. Strain NRRL 328 had the highest KDG aldolase activity (See Table 1) and was selected for further growth and purification.

TABLE 1

KDG Aldolase Activity of *Aspergillus niger* lysates

|  | Decrease in A340 nm per minute |
|---|---|
| No KDG | 0.00562 |
| No NADH | 0.00058 |
| No Enzyme | 0.00088 |
| Strain NRRL 322 | 0.01634 |
| Strain NRRL 328 | 0.02392 |
| Strain NRRL 566 | 0.01086 |
| Strain NRRL 599 | 0.00696 |
| Strain NRRL 2270 | 0.0197 |

Example 3

Purification of an *Aspergillus niger* KDG Aldolase

*Aspergillus niger* strain 328 was inoculated into 200 mL PD broth in 4×1 L flasks and grown at 30° C. and 240 rpm for 46 hours. Mycelia were harvested by centrifugation and then resuspended in 200 mL Czapek Dox broth with 5% Na gluconate as the sole carbon source and returned to the incubator for 44 hours. Mycelia were harvested and sonicated to prepare a lysate. The sample was heat treated for 15 minutes at 60° C. and the precipitated protein was removed by centrifugation at 10,000 g for 15 minutes at 4° C. A volume of 200 mL supernatant was mixed with an equal volume of cold acetone (−15° C.) and mixed gently for 10 minutes at 4° C. The precipitate was removed via centrifugation and discarded and another 200 mL of cold acetone was added to form a second precipitate.

This second precipitate was dried, then resuspended in buffer and loaded onto two 5 mL DEAE fast flow columns setup in tandem. The mobile phase was 10 mM Potassium Phosphate pH 7.7 and proteins were eluted with a gradient from 0 to 0.5M NaCl over 40 column volumes. The OD was monitored at 280 nm and fractions were collected and assayed for KDG dehydratase activity as described previously. The most active fractions were then pooled for proteomic analysis.

Example 4

Identification of a KDG Aldolase Via LC-MS/MS Proteomics

Samples from the original lysate, the $2^{nd}$ acetone precipitate, and the most active fractions from the DEAE column were analysed for protein content via trypsin digest and LC-MS/MS. The sample containing the most active fractions contained an enriched abundance of peptides for a protein annotated in the *Aspergillus niger* genome database, as an uncharacterized protein with accession number G3Y6P2 (SEQ ID NO:1). Upon further investigation, another annotation for same sequence was dihydropicolinate synthase in PFAM, a class of enzymes that catalyzes the condensation of L-aspartate-4-semialdehyde and pyruvate to 4-hydroxy-tetrahydropicolinic acid. It was noted that the reverse of this reaction is quite similar to the activity that had been observed where cleavage of KDG resulted in production of pyruvate. Upon further investigation, protein G3Y6P2, had ~76% sequence identity with a putative 4-hydroxy-2-oxoglutarate aldolase from *Aspergillus udagawae*. To further verify that this was the protein sequence associated with the KDG aldolase activity, the protein was re-purified using a similar protocol where the acetone precipitation was excluded to improve the purification yield and a higher resolution MonoQ column was used instead of a DEAE column. The most active fractions were analyzed on an SDS-PAGE gel and the prominent band in the active fractions was excised. A trypsin digest and LC-MS/MS confirmed that the prominent band was in fact G3Y6P2.

```
                                             SEQ ID NO: 1
>tr|G3Y6P2|G3Y6P2_ASPNA Uncharacterized protein
OS = Aspergillus niger (strain ATCC 1015/CBS
113.46/FGSC A1144/LSHB Ac4/NCTC 3858a/NRRL 328/
USDA 3528.7) GN = ASPNIDRAFT_214527 PE = 3 SV = 1
MAITPRPLKPGIYVPTVAFFTSPNEDLDLSTTALHATYLAQAGVTGLVVQ

GSNGEAVHLSREERNLITSTTRRALDSHAPSAPLIVGCGAASTRETIQLC

QDAAASGGDYTLILPPSYYKSLLSPKDLLDHFRLVASASPIPILVYNFPG

ASSGLDLSSDDILALAEHPNIVGVKLTCGNTGKLARIAAAAEPGFMTFGG

SADFTLQTLVAGGHGVIGGVANLIPRLSVRVMELYQAGQVEEAQRLQAIV

ARADWQAIKGGFVAVKSALQTYRGYGALPRRPCVVPSEAQATAWKDSFAE

AMELERQLEKQA

SEQ ID NO: 2
ATGGCCATTACACCCCGCCCCCTCAAACCCGGCATCTACGTCCCAACCGT

CGCCTTCTTCACCTCTCCCAACGAAGACCTCGACCTCTCCACCACCGCCC

TCCACGCCACCTACCTCGCTCAAGCCGGCGTCACCGGTCTAGTCGTGCAA

GGCAGCAACGGTGAAGCCGTCCACCTCAGCCGCGAAGAGCGCAACCTCAT

CACTTCCACCACCCGTCGCGCTCTCGACTCTCACGCCCCCTCCGCCCCGC

TCATCGTCGGCTGCGGCGCCGCCTCCACCCGCGAGACCATCCAGCTGTGC

CAAGACGCCGCCGCCTCCGGAGGCGACTATACCCTGATCCTCCCTCCCTC

CTACTACAAATCCCTCCTCTCTCCCAAGGACCTTCTTGATCACTTCCGCC

TCGTCGCCTCCGCCTCCCCCATCCCCATCCTGGTGTACAACTTCCCCGGC

GCCTCTTCGGGCCTGGACCTCTCCTCCGACGACATCCTCGCCTTGGCGGA

GCACCCCAACATCGTCGGCGTGAAGCTGACCTGTGGAAACACGGGTAAAC
```

-continued

```
TGGCGCGCATTGCCGCCGCCGCCGAACCCGGTTTCATGACCTTTGGTGGT

TCCGCTGATTTCACTCTCCAGACGCTGGTGGCAGGCGGTCATGGAGTGAT

TGGCGGCGTGGCGAACCTGATCCCTCGTTTGAGTGTGCGCGTGATGGAGC

TGTATCAGGCGGGACAGGTCGAAGAGGCCCAGCGGTTGCAGGCCATTGTA

GCGCGTGCGGACTGGCAGGCTATCAAGGGTGGTTTTGTAGCGGTGAAGAG

TGCGTTGCAGACGTACCGCGGATACGGAGCATTGCCGAGACGGCCGTGTG

TGGTGCCGTCAGAGGCGCAGGCGACGGCGTGGAAGGATTCTTTTGCGGAG

GCTATGGAGCTGGAGAGACAGTTAGAGAAGCAGGCCTAG
```

Example 5

Expression of Putative KDG Aldolase EHA21505 in *E. coli*

To ensure the proper expression of the *Aspergillus niger* KDG aldolase in *E. coli*, an *E. coli* codon-optimized gene encoding protein G3YP2, referred to here as EHA21505 or 21505, was obtained (SEQ ID NO: 3) (Genewiz, South Plainfield, N.J.).

SEQ ID NO: 3
```
ATGGCAATTACCCCTCGCCCGCTGAAGCCGGGCATTTACGTGCCGACCGT

TGCCTTTTTCACCAGCCCGAATGAGGACCTGGACCTGAGCACCACCGCAC

TGCATGCAACCTATCTGGCACAGGCAGGTGTGACCGGCCTGGTTGTGCAG

GGTAGCAATGGTGAAGCCGTGCATCTGAGCCGTGAGGAGCGTAACCTGAT

TACAAGCACCACCCGCCGTGCACTGGATAGCCATGCCCCGAGTGCCCCGC

TGATCGTTGGTTGCGGTGCAGCAAGCACCCGCGAAACCATTCAGCTGTGT

CAAGATGCAGCCGCCAGTGGCGGCGACTATACTCTGATCCTGCCGCCGAG

CTACTACAAAAGCCTGCTGAGTCCGAAGGATCTGCTGGACCATTTTCGCC

TGGTTGCCAGCGCAAGCCCGATTCCGATTCTGGTGTATAACTTTCCGGGC

GCCAGTAGCGGTCTGGACCTGAGTAGCGATGATATTCTGGCACTGGCAGA

GCATCCGAACATTGTGGGCGTGAAACTGACCTGCGGTAACACAGGCAAAC

TGGCACGTATCGCAGCCGCAGCAGAACCGGGTTTTATGACCTTTGGCGGT

AGTGCCGACTTTACCTTACAGACCCTGGTTGCCGGTGGTCATGGTGTGAT

TGGCGGCGTGGCAAATCTGATTCCGCGCCTGAGCGTTCGTGTTATGGAGC

TGTACCAGGCAGGTCAGGTGGAAGAAGCCCAGCGTCTGCAGGCCATTGTG

GCACGTGCCGACTGGCAGGCCATTAAAGGCGGTTTTGTGGCCGTGAAAAG

CGCCCTGCAGACCTACCGCGGTTATGGTGCACTGCCGCGTCGTCCGTGTG

TGGTGCCTAGCGAAGCACAGGCCACCGCATGGAAAGATAGCTTTGCCGAG

GCTATGGAACTGGAACGCCAGCTGGAAAAACAAGCCTAA
```

This gene was cloned in the NcoI-HindIII sites of expression vector pTrcHis2B (Thermo Fisher Scientific, Waltham, Mass.). This plasmid was named pTrc-An21505.

Plasmid pTrc-An21505 was transformed into BL21 *E. coli* competent cells (EMD Millipore; Billerica, Mass.), following the protocol provided by the vendor. The BL21 strain containing plasmid was named *E. coli* 21505. Vector pTrcHis2 was also transformed into BL21 as a control. To evaluate KDG aldolase activity in *E. coli* the mentioned 2 strains were inoculated into shake flasks containing auto-induction liquid media Studier ZYM-5052 (Teknova; Hollister, Calif.). Flasks were incubated in a shaking incubator for 24 hours at 30° C. and 110 rpm. After cultivation, cultures were centrifuged at 12500 g for 20 minutes and the pellets were stored at −80° C. overnight. To prepare cell-extracts, pellets were thawed and lysed in the following solution: 7 ml per gram of 10 mM sodium phosphate buffer, pH 7.3, mixed with 7.5kU rLysozyme per ml of buffer, 1 ul benzonase nuclease (EMD Millipore, P/N 70746) per ml of buffer. The mixtures were incubated in a water bath for 10 minutes at 60° C. then centrifuged at 10000 g for 20 minutes. The lysates were tested for KDG aldolase activity using the method previously described, with modifications for a plate-based assay. Lysates were buffer exchanged in 10 mM sodium phosphate buffer (pH 7.7) using a PD-10 column. The assay reactions were monitored in a 96-well Costar plate and a reading was taken every 30 seconds for 20 minutes. Lysate from *Aspergillus niger* strain NRRL 566 was included in the assay as a positive KDG aldolase activity control. As shown in Table 2, the *E. coli* strain expressing the 21505 gene (BL21+pTrc-An21505 lysate) had higher activity than the *E. coli* empty vector strain (BL21+pTrcHis2b) and background controls. The *E. coli* empty vector strain (BL21+pTrcHis2b) had minimal activity only slightly above the "No KDG" background control. The *Aspergillus niger* NRRL 566 positive control had the highest KDG aldolase activity.

TABLE 2

KDG Aldolase Activity in *Aspergillus niger* and *E. coli* lysates with, and without the 21505 gene

| Description | Decrease in Absorbance at 340 nm per minute |
| --- | --- |
| No KDG added | 0.00296 |
| No NADH added | 0.00071 |
| No cell lysate added | 0.00198 |
| *A. niger* NRRL 566 lysate | 0.01440 |
| BL21 + pTrc-An21505 lysate | 0.00851 |
| BL21 + pTrcHis2b lysate | 0.00323 |

Example 6

Inactivation of EHA21505 Gene in *Aspergillus Niger*

Preparation of Deletion Cassette

A deletion cassette was constructed so that the DNA can integrate into the genome at the 21505 locus, thus substituting the 21505 gene with the hygromycin B resistance gene. Regions approximately 1000 bp upstream and downstream of 21505 were cloned and ligated to the pBluescriptSK+plasmid (Agilent; Santa Clara, Calif.). The region upstream of gene 21505 was cloned using the following primers:

SEQ ID NO: 4
5'-CTTGATATCGAATTCGACGAGGTGGGATTATTGCTG-3' and

SEQ ID NO: 5
5'-CATCGTTTGCATCATCAGGGGATGGG-GAGAATGCG-3', which was designed to introduce an EcoRI restriction site. The downstream region of 21505 was cloned using the following primers:

SEQ ID NO: 6
5'-CACGGCTCAGACTCTCCCACATCTTCTACATACCCATC-3' and

SEQ ID NO: 7
5'-CTAGTGGATCCCCCGGGCGC-CTCATATTCCTCGATGC-3'.

This primer also introduced an XmaI restriction site. A gene for hygromycin B resistance, using the *Aspergillus niger* ubiquitin promoter and ubiquitin terminator, was placed between the upstream and downstream fragments (Punt, et al. 1987). The deletion cassette comprising of the two DNA fragments and the hygromycin B resistance gene was assembled via overlap PCR using In-Fusion HD Cloning Plus kit (Clontech; Mountain View, Calif.).

The DNA sequence of the complete deletion cassette is shown below:

SEQ ID NO: 8
CTAAATTGTAAGCGTTAATATTTTGTTAAAATTCGCGTTAAATTTTTGTT
AAATCAGCTCATTTTTTAACCAATAGGCCGAAATCGGCAAAATCCCTTAT
AAATCAAAAGAATAGACCGAGATAGGGTTGAGTGTTGTTCCAGTTTGGAA
CAAGAGTCCACTATTAAAGAACGTGGACTCCAACGTCAAAGGGCGAAAAA
CCGTCTATCAGGGCGATGGCCCACTACGTGAACCATCACCCTAATCAAGT
TTTTTGGGGTCGAGGTGCCGTAAAGCACTAAATCGGAACCCTAAAGGGAG
CCCCCGATTTAGAGCTTGACGGGGAAAGCCGGCGAACGTGGCGAGAAAGG
AAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACA
GGGCGCGTCCCATTCGCCATTCAGGCTGCGCAACTGTTGGGAAGGGCGAT
CGGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTTG
TAAAACGACGGCCAGTGAGCGCGCGTAATACGACTCACTATAGGGCGAAT
TGGGTACCGGGCCCCCCCTCGAGGTCGACGGTATCGATAAGCTTGATATC
GAATTCGACGAGGTGGGATTATTGCTGGCCAGCGGGCGGCGCGTCGAGGT
CCGCCGGCGCAGGGGATGATGAGACGAGAGTTTGTAGGGCGTGGCAGCTG
AGGAGGACGAGTTCTCCGTCGTGGTGGTGTCCAGCAGATCGGGGAGCTT
TTGCGACGGCGCGATGACGAGTGAGTCTGGAGACGAGCTCGCTTTGCAGG

-continued

AGGCTCGGAGTCCGGCTGGTCGGGGGAATGGCCGTGATGAGGATCTCGTC
GCAGGGAGACACGGACAGGCATCAGGGTGGTGGAGGTCATTCGGGAGGAT
CGAGGAGGGGAGAGGAATTGAGACGTGGGGGGAAAGAAAGGTCAGGAGGG
ATGCGTGCACGGCATGTCAGGGCCAGTCGGGGGCAATTCGGAGGATTGAA
GTTGGCAGGAGGTTTTTTGGGCGAAGCTGAAGCACTCGAGAATCGCAGCT
GCAGGTCTGGATGTGTTCCGGATTGGGAGGAGTTGAAAGTTGTATCTTTA
CGGATACCGCAGCAGGTATGTCTCAGTACCTGACAGGACAGGTGTTACCG
CCAGGATGTATGATACCTGTCACAACGATACCTCACTGGACTAGCTTAAC
ATACATACATACATCATACATCTTCACATCTTCACTCTTCTTCTACTGCA
TCAACTTCTGCGTGAAGCACTTCTAATTCATCCACCCCATTCACTCCTTT
TCCGGCTCACCTCATTTCTCCGAGGAACCAATTCTCCGACGACTACCCCA
TTCCTCTACCATAATGCTTCCCAGCACGACGTGGGGGTGGGAGCTCCCCT
GACTTGCCATAGGAGGGGATCTGCTGGAGAGAGTGTGGGGTGCGTGGGGG
TTTGGCTGGATTGTTTTCTGCTCGACGCTGTCTGGATGGAGTCAACCGGC
TCAATGTCCGACTCTCTCCCAACTTAACTGGAACTGTTTCCCCTCTTAGC
CACCCACTGGCTTGCTTTCTTATATATCATGGCAACGACTTCCTCGTTGC
TTTCCATCTGTCCTCCTCTTCTTCCTCCTCCTCCTTCCTCTTCCCCCGCA
TTCTCCCCATCCCCTGATGATGCAAACGATGAGCTGGTATATGACACTGG
AATGCATGCAGTCATGGATACGATTCAGTGGGTGCCGGGCCAAAAGCGGG
GCATTCCGGATGCGACGATCACCTGACCCATCTCCAGCCGCTAGCGATGG
CCTAAGGCCACTTCCCGAGGCCGCGCCGTCGAGATAACAGCTGGAGAGGA
TCCCCTTCCCCCATCCTCCATCCTCCGATAAGGAATGCCCCAACTCACA
CGTCATCGCCGTTGCTGCCGCCGCAAGGCCAGTTGTCGCATTCCCTCTCT
GATCATCACCCCCCAGTTTACCTGGTGAGATGATACGAATTATCAATGAG
AAGGCAAACAATATATAGACAGCAGAAACTCCGAGTTTCAACGGGTTCTA
TTTCAGGAACACGGCTGCGGTCTGGATTGGGTCGGGCTGAGATACCGACT
GGTGGCGTCAGTGGCGGGTACGGACGGAGTCGTCCTGTCCGCTCGTAGAC
GCTTCCCCCGGACTGATATCAGGCCCCGGCAACCAACTGGCTTCGATTCC
CCTCCCATGGCAGCAGCAGTGCCTACCACATGGGATCAGGCTTTTGCCTG
TTGTTCTAAGTTTTGCAGACAGAATTTTCGTATGCGTTACCACTCTTTTT
CTTTCAGCGACCATTCCCGTTGTAGTTGTAAACCCAATAATAGGTGGCTG
CCGTGGGAGCCTGAGTCAACCCAACCAGAACCTTTCTAGTAGATTCTCCC
TCCCAAGCGCTTCAGCAACGAAGCGTATTGGAGAACCAAATGACGCAGAC
CAGGCGGATTCCGGCGCAATAGCCGGATGGCAAGGGAATCCCCCAGGAGG
TGCCAGAAGCGTCGCCCGAAAGGTACTTCGTCTGACAGGCTAACACCGCT
CGGGCCAAGGTCCCTGCTGCTCTTTTCCCTTTATTGCGACTTGACCTCTA
AGCCATTCCCTTGCATCACGTTATCTCACTGACCGATCCTCTGACTAAGG
CGCTTCGCCTCCGCCTCCCCTCATTCACCTCCTCTCCTGACTACTTAAGC
CTTCTCTTCCTTCCTTCCTCTACCAACCCTCCTTCATCCCTCATACCTCT
CATCCTACCACTCACCTTCCGCGCATCGCCATCTGCGATTCTCTCCACAA
CAACTCCACCTAATCACATACACCATTAACTGCGCTTCTACAACATGAAA

```
AAGCCTGAACTCACCGCGACGTCTGTCGAGAAGTTTCTGATCGAAAAGTT
CGACAGCGTCTCCGACCTGATGCAGCTCTCGGAGGGCGAAGAATCTCGTG
CTTTCAGCTTCGATGTAGGAGGGCGTGGATATGTCCTGCGGGTAAATAGC
TGCGCCGATGGTTTCTACAAAGATCGTTATGTTTATCGGCACTTTGCATC
GGCCGCGCTCCCGATTCCGGAAGTGCTTGACATTGGGGAATTCAGCGAAA
GCCTGACCTATTGCATCTCCCGCCGTGCACAGGGTGTCACGTTGCAAGAC
CTGCCTGAAACCGAACTGCCCGCTGTTCTGCAGCCGGTCGCGGAGGCCAT
GGATGCGATCGCTGCGGCCGATCTTAGCCAGACGAGCGGGTTCGGCCCAT
TCGGACCGCAAGGAATCGGTCAATACACTACATGGCGTGATTTCATATGC
GCGATTGCTGATCCCCATGTGTATCACTGGCAAACTGTGATGGACGACAC
CGTCAGTGCTTCCGTCGCGCAGGCTCTCGATGAGCTGATGCTTTGGGCCG
AGGACTGCCCCGAAGTCCGGCACCTCGTGCACGCGGATTTCGGCTCCAAC
AATGTCCTGACGGACAATGGCCGCATAACAGCGGTCATTGACTGGAGCGA
GGCGATGTTCGGGGATTCCCAATACGAGGTCGCCAACATCTTCTTCTGGA
GGCCGTGGTTGGCTTGTATGGAGCAGCAGACGCGCTACTTCGAGCGGAGG
CATCCGGAGCTTGCAGGATCGCCGCGGCTCCGGGCGTACATGCTCCGCAT
TGGTCTTGACCAACTCTATCAGAGCTTGGTTGACGGCAATTTCGATGATG
CAGCTTGGGCGCAGGGTCGATGCGACGCAATCGTCCGATCCGGAGCCGGG
ACTGTCGGGCGTACACAAATCGCCCGCAGAAGCGCGGCCGTCTGGACCGA
TGGCTGTGTAGAAGTACTCGCCGATAGTGGAAACCGACGCCCCAGCACTC
GTCCGAGGGCAAAGGAATAGTGCCTTATTTTGATCTTTCTTCTTTAGCAC
GGCTCATCTACGGTTGAGTGGCCTGCATGGCGTTGGGACGGTTGTTTTAT
CGGTTTTATGACACGGATAAATTGGGCATACCTTAGGGTCACCATCTTCT
ATGGTGCCTTGCGACATTCTTTCACCTAGGAATCAATCCAATAATTATAT
TCCACCTGATATCTTGCTTGCACTGTTTCCTGTAGATTTAGTAGGACCGC
CCGAAGTAGACCGCCACGCTAGCATAGACGTGGTCCACATGCAATTCAGG
ACGGCGTCCACCCCCTTACAGATCGTATGCGAAGAAATTAACTAGATAAT
AAAATGGCTTCATCTTCATCTTCATCTACCTATACAATCGCTAACAAGGA
ACTAATAGACATCGCAGGTGAGTCACCGTCTTCACCACCCGTATCTTAGC
ACGTGACTATACCGTCCCAAGGCGGCGTGGGACAGGAAAGTAGCTTCCAT
TCATGAACTCGACCTGAGAGAGCAGTTGCAGACGTGTAACACGCTGGAGA
TGTGAGCATCAGTCGTGATGCCCTCCTACTTCTACCACATTGCGATCGAA
TTATTTGCTCGCCCGCACTCTGACCTCCATGGCACCTACCCAGGCGTGGA
CAAGCACTCGACATCGCTATCCTTCGACTCCGCATGCGAAGCTCTACCCC
CGTTCCAGAAGCGCCCCGACACTCACCGTGGGCACATCGATCCTCTCGT
CATCAAGCGCATGGGAAACACCCACGCCCCTCATCCAACACTTTCGCCGA
AACCCACGGCTCAGACTCTCCCACATCTTCTACATACCCATCATCATCAT
CATCATCTATACAAACGGCAACACCAAATACGAATCAAACTCCACCCCAC
AATGAACCTCATGCACCTGCTCTTTCTCCCCCACATCCCCTCCCGATCCC
TCCCCTTCCACCGGACCAAACTCCACCTCCGGATAACACAAATCACGCCC
CGCCACCCTCAACATAATCCCCTCCCCAGCACCAAACACCATTCCCATCG
GCCACAACGTAATATCAATCGGCACGATCTTTCCCGCCGGGATGCTCTCC
GCCCGATCATGTCTATACACAATCTCATGCTCTGTCGAGAGCGTCTCGTC
CCGTGTGACGGCGTGCGACGCACGCAGGAACCCCTGCGGTCCGAGCGTCT
TGGCTGTGTTGACGTTGGGGACGGCGTCAACGGGCACGGGACACGGGTAG
TTGAGGTGTTCGAGAAGCGTGCCGGTGGCGGAGATCTTGCGGATTTGCAC
GATGATGTCCATGTCTGTGTGGTGGGGGGTGGAGAGCCACAGATGTACGC
GGGGGTACCCGGCTAACTGAGTGGGGGTGGGGAAGTGGAGGGTGAAGTCC
TATTATTTGTTAGGAGATATTGAGAGAGAGGGTATGTTAAGGGGGAGACG
TACGGAGGTGCCATGGAGGGCGGAATGGGTTGTTGAGGTGACTGTGCTTG
GGAGAGAGGGTTGGAGGGTCTTGGTTGATGCGTTGAGGTAGAATTTCTTG
AGCTCCTGCCGGGTTAATGGGTAGGTATGTTCGGGGCGTTCGAGGATGGT
TGGCACAGAGCTGCCTTCGAATCCAAGGAGGGAGAGGCGCACCGGTGGTG
TGCTTTCCCAGTCGTTGGGTGTGTTCTTAAGATAGCGGTCGAAGAAACGA
GAGAGGTCGTCGACCATCTCGGGTCGGTATAGATCGTACCATTCTTGGTA
TGGGTGCACGCGGAGCCATTTTCGGGTGCTCTGGGCGGTGCGGAAGGTTT
CGAAGGAGCCGCGCGTGTGCAGCATCGAGGAATATGAGGCGCCCGGGGA
TCCACTAGTTCTAGAGCGGCCGCCACCGCGGTGGAGCTCCAGCTTTTGTT
CCCTTTAGTGAGGGTTAATTGCGCGCTTGGCGTAATCATGGTCATAGCTG
TTTCCTGTGTGAAATTGTTATCCGCTCACAATTCCACACAACATACGAGC
CGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCG
TGCCAGCTGCATTAATGAATCGGCCAACGCGCGGGGAGAGGCGGTTTGCG
TATTGGGCGCTCTTCCGCTTCCTCGCTCACTGACTCGCTGCGCTCGGTCG
TTCGGCTGCGGCGAGCGGTATCAGCTCACTCAAAGGCGGTAATACGGTTA
TCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATA
GGCTCCGCCCCCTGACGAGCATCACAAAAATCGACGCTCAAGTCAGAGG
TGGCGAAACCCGACAGGACTATAAAGATACCAGGCGTTTCCCCCTGGAAG
CTCCCTCGTGCGCTCTCCTGTTCCGACCCTGCCGCTTACCGGATACCTGT
CCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTC
TTGAGTCCAACCCGGTAAGACACGACTTATCGCCACTGGCAGCAGCCACT
GGTAACAGGATTAGCAGAGCGAGGTATGTAGGCGGTGCTACAGAGTTCTT
GAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGA
TCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTT
CTACGGGGTCTGACGCTCAGTGGAACGAAAACTCACGTTAAGGGATTTTG
GTCATGAGATTATCAAAAAGGATCTTCACCTAGATCCTTTTAAATTAAAA
```

-continued

```
ATGAAGTTTTAAATCAATCTAAAGTATATATGAGTAAACTTGGTCTGACA
GTTACCAATGCTTAATCAGTGAGGCACCTATCTCAGCGATCTGTCTATTT
CGTTCATCCATAGTTGCCTGACTCCCCGTCGTGTAGATAACTACGATACG
GGAGGGCTTACCATCTGGCCCCAGTGCTGCAATGATACCGCGAGACCCAC
GCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGT
ATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTG
CATAATTCTCTTACTGTCATGCCATCCGTAAGATGCTTTTCTGTGACTGG
TGAGTACTCAACCAAGTCATTCTGAGAATAGTGTATGCGGCGACCGAGTT
GCTCTTGCCCGGCGTCAATACGGGATAATACCGCGCCACATAGCAGAACT
TTAAAAGTGCTCATCATTGGAAAACGTTCTTCGGGGCGAAAACTCTCAAG
GATCTTACCGCTGTTGAGATCCAGTTCGATGTAACCCACTCGTGCACCCA
ACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATG
TTGAATACTCATACTCTTCCTTTTTCAATATTATTGAAGCATTTATCAGG
GTTATTGTCTCATGAGCGGATACATATTTGAATGTATTTAGAAAAATAAA
CAAATAGGGGTTCCGCGCACATTTCCCCGAAAAGTGCCAC
```

Before transformation into *Aspergillus niger*, the deletion cassette was amplified by PCR with iProof polymerase (Bio-Rad; Hercules, Calif.).

*Aspergillus niger* Transformation

Transformations were performed according to the method of Yelton, et al. (1984) with some modifications. $1 \times 10^6$ NRRL 566 spores/mL were used to inoculate *Aspergillus* Complete Medium (ACMU2; 1% yeast extract, 1% bacto peptone, 2.5% glucose, 11 mM KH2PO4, 7 mM KCl, 2 mM MgSO4, 5 mM uridine, 5 mM uracil, 1× Hutner's trace elements) and grown in a shaking incubator for 17 hours at 30° C. and 250 rpm. Mycelia was collected via miracloth filtration, washed with osmotic medium (OM; 1.2M MgSO4, 10 mM sodium phosphate, pH 5.8), and transferred to a 1 L flask to be combined with a variation of the enzyme cocktail described by de Bekker, et al. (2010). The cocktail comprised of 0.15 U/mL chitinase from *Streptomyces griseus* (Sigma, P/N C6137), lysing enzymes from *Trichoderma harzianum* (Sigma, P/N L1412), β-glucuronidase from *Helix pomatia* (Sigma P/N G1512), and OM at 8 mL per gram of biomass. Protoplasts were generated by placing the culture in a shaking incubator for 2.75 hours at 30° C. and 100 rpm. Protoplasts were then combined with an equal volume of ST buffer (0.6M sorbitol, 100 mM Tris-HCl, pH7.5). The mixture was centrifuged at 4000 g for 15 minutes and the resulting protoplast layer was then transferred to a new bottle. The pellet was suspended in the residual buffer and the procedure was repeated to collect any remaining protoplasts. The protoplasts were then washed twice using cold STC buffer (1M sorbitol, 10 mM Tris-HCl, pH 7.5, 10 mM CaCl$_2$)) and a centrifuge speed of 4100 g for 15 minutes. A protoplast suspension was made with 10% total volume of PTC (60% PEG 4000, 50 mM CaCl$_2$), 10 mM Tris-HCl pH 7.5), 10% total volume of 200 mM aurintricarboxylic acid (Gielesen, B. 2013) and 80% total volume protoplast suspension mixed with STC to bring the final concentration to $4 \times 10^7$ protoplasts/mL.

The PCR-amplified knockout cassette DNA was mixed with the protoplast suspension in a round bottom tube, and incubated on ice for 20 minutes. PTC (60% w/v PEG 4000; 10 mM Tris-HCl, pH 7.5; 50 mM CaCl$_2$)) was slowly added and the tubes were incubated at room temperature for 10 minutes. Cold STC was then added and mixed, followed by a centrifugation at 3220 g for 10 minutes at 4° C. The pellet was suspended in residual supernatant and plated onto selection plates (PDA, 1.2M sorbitol, hygromycin 500 µg/ml, 5 mM uridine, 5 mM uracil). After 5 days incubation at 30° C., hygromycin resistant transformants were transferred to secondary selection plates (PDA, hygromycin 500 µg/ml, 5 mM uridine, 5 mM uracil) and incubated for 4 days at 30° C.

Thirty-four fungal colonies from the secondary selection plates were analyzed by PCR for the deletion of the 21505 gene using Phire Plant Direct PCR Master Mix (ThermoFisher, Waltham, Mass.). Primers targeted to regions upstream and downstream of the 21505 gene, 5'-TCGTTGCTTTCCATCTGTCC-3' (SEQ ID NO:9) and 5'-GTGGGGTGGAGTTTGATTCG-3' (SEQ ID NO:10), respectively, produced a 3.1 kb product when the knockout cassette was present and a 1.2 kb product when the 21505 gene was still present. A second PCR was performed to test for the correct targeted integration location of the knockout cassette. Primers targeted the hygromycin B resistance marker, 5'-CGATCAGAAACTTCTCGACAGAC-3' (SEQ ID NO:11), and the region upstream of the 21505 flanking region, 5'-GATGTGATAGTGGGGGTGGAATC-3' (SEQ ID NO:12), producing a 2.3 kb product. Four colonies showed the insertion of the knockout cassette in the targeted location to confirm the deletion of the 21505 gene and three isolates were selected for further analysis.

Example 7

Measurement of KDG-Aldolase Activity in *Aspergillus niger* Knockout Strain

Cell lysates from wild type *Aspergillus niger* strain and three knockout strain isolates were prepared using a bead beater and lysis buffer (Zymo Research, Irvine, Calif., P/N D6001), and tested for KDG aldolase activity using the method previously described for the *E. coli* 21505 activity assay described in Example 5. As shown in Table 3, wild type *Aspergillus niger* strain NRRL 566 had visible KDG aldolase activity (See Table 3) while the knockout strains only showed absorbance values similar to the "No KDG" background absorbance.

TABLE 3

KDG Aldolase Activity of *Aspergillus niger* parent and knockout strains

| | Decrease in Absorbance at 340 nm per minute |
|---|---|
| No KDG | 0.00116 |
| No NADH | 0.00008 |
| No Enzyme | 0.00091 |
| Wild-type Parent Strain | 0.01716 |

TABLE 3-continued

KDG Aldolase Activity of *Aspergillus niger*
parent and knockout strains

| | Decrease in Absorbance at 340 nm per minute |
|---|---|
| Knockout Strain Isolate A | 0.00179 |
| Knockout Strain Isolate B | 0.00151 |
| Knockout Strain Isolate C | 0.00140 |

Example 8

Quantification of KDG

Samples of culture supernatants were analyzed for Gluconate and KDG content using a Dionex ICS-5000 Ion Chromatography System. The instrument was equipped with a Dionex IonPac AS11-HC column and an AG11 guard column. The following potassium hydroxide gradient generated by the eluent generator at 2 mL/minute was utilized to separate KDG from gluconate for quantitation: 5 mM to 20 mM in 2 minutes, 20 mM to 50 mM in 1 minute, 50 mM for 2 minutes. The column was re-equilibrated to 5 mM for 3 minutes. Suppressed conductivity was used for gluconate and KDG detection utilizing Dionex ASRS-Ultra 4 mm AutoSuppressor at 248 mA in recycle mode. The conductivity cell was set to 35° C., the detector compartment to 15° C. and the column compartment to 30° C. Solid standards for gluconate and KDG were dissolved in water to 20 mM and combined to a stock concentration of 10 mM each. The stock standard solution was further diluted with water to yield the following concentrations: 5, 2.5, 1.25, 0.625, 0.313, 0.156 and 0.078 mM. Injection volume was 10 µL for all samples and standards. All fermentation samples were diluted 1:50 in water prior to injection. Baseline separated peaks for gluconate and KDG eluted from the column at 2.28 minutes and 2.52 minutes respectively. Peak integration was achieved by applying software specific algorithm. Sample concentrations were determined based on standard curve fit.

Example 9

Production of KDG by *Aspergillus niger* Strains

The three isolates containing the 21505 knockout were grown in gluconate-based media and evaluated along with the parent strain to determine if KDG was accumulated. For such a purpose, spores from the *Aspergillus niger* parent strain NRRL 566 and three different isolates of the 21505 knockout strain were used to inoculate starter cultures of potato dextrose broth, 5 mM uridine, and 5 mM uracil in shake flasks. The flasks were grown for 48 hours in a shaking incubator at 30° C. and 220 rpm. The biomass growth was then transferred to Czapek Dox broth with 3% sodium gluconate as the sole carbon source in shake flasks. The cultures were grown in a shaking incubator for 4 days at 30° C. and 220 rpm. Culture broths were then collected and centrifuged at 7500 g for 20 minutes to remove any residual biomass. Concentrations of Gluconate and KDG in the supernatants were determined as described in Example 8. As shown in Table 4 below, only the 3 knockout strains accumulated KDG in significant amounts, indicating that gene EHA21505 is involved in KDG metabolism in *Aspergillus niger*.

TABLE 4

KDG Accumulation in cultures of *Aspergillus niger* strains

| Sample | KDG (mM) |
|---|---|
| Growth Media | 0 |
| Lysate from Knockout isolate A | 11.4 |
| Lysate from Knockout isolate B | 10.2 |
| Lysate from Knockout isolate C | 10.8 |
| Lysate from *A. niger* NRRL 566 wild-type | 0 |

TABLE 5

BLAST Results obtained 07-19-2017 using sequence EHA21505.

| Annotation | Identity | Accession |
|---|---|---|
| Hypothetical protein ASPNIDRAFT_214527 [*Aspergillus niger* ATCC 1015] | 100% | EHA21505 |
| Unnamed protein product [*Aspergillus niger*] | 99% | CAL00542 |
| Dihydrodipicolinate synthase-like protein [*Aspergillus niger* CBS 513.88] | 99% | XP_001398069 |
| Hypothetical protein ASPBRDRAFT_195814 [*Aspergillus brasiliensis* CBS 101740] | 98% | OJJ71649.1 |
| Dihydrodipicolinate synthetase family protein [*Aspergillus kawachii* IFO 4308] | 98% | GAA89280 |
| Dihydrodipicolinate synthetase family protein [*Aspergillus luchuensis* | 98% | GAT28880 |
| Hypothetical protein ASPTUDRAFT_56088 [*Aspergillus tubingensis* CBS 134.48] | 98% | OJI84140 |
| hypothetical protein ASPFODRAFT_45842 [*Aspergillus luchuensis* CBS 106.47] | 98% | OJZ86393 |
| dihydrodipicolinate synthetase family protein [*Aspergillus niger*] | 98% | GAQ43461 |
| Hypothetical protein ASPCADRAFT_46975 [*Aspergillus carbonarius* ITEM 5010] | 90% | OOF96363 |
| Hypothetical protein ASPACDRAFT_1889470 [*Aspergillus aculeatus* ATCC 16872] | 81% | XP_020054543 |
| Hypothetical protein ASPACDRAFT_1889470 [*Aspergillus aculeatus* ATCC 16872 | 81% | OJJ98203 |
| Hypothetical protein ARAM_004705 [*Aspergillus rambellii*] | 72% | KKK21095 |
| Hypothetical protein ASPWEDRAFT_44050 [*Aspergillus wentii* DTO 134E9] | 72% | OJJ32031 |

TABLE 5-continued

BLAST Results obtained 07-19-2017 using sequence EHA21505.

| Annotation | Identity | Accession |
|---|---|---|
| Conserved hypothetical protein [Aspergillus terreus NIH2624] | 77% | XP_001210210 |
| Conserved hypothetical protein [Aspergillus terreus NIH2624] | 77% | EAU38770 |
| Putative Dihydrodipicolinate synthetase family protein [Aspergillus calidoustus] | 74% | CEL08355 |
| Hypothetical protein AOCH_003138 [Aspergillus ochraceoroseus] | 72% | KKK19949 |
| Dihydrodipicolinate synthetase family protein [Aspergillus clavatus NRRL 1] | 76% | XP_001276612 |
| Dihydrodipicolinate synthetase family protein [Aspergillus clavatus NRRL 1] | 76% | EAW15186 |
| Hypothetical protein PENSUB_13354 [Penicillium subrubescens] | 72% | OKO90637 |
| Probable 4-hydroxy-2-oxoglutarate aldolase, mitochondrial [Aspergillus udagawae] | 76% | GAO82082 |
| Putative 4-hydroxy-2-oxoglutarate aldolase, mitochondrial [Aspergillus cristatus] | 71% | ODM19761 |
| Hypothetical protein AN1503.2 [Aspergillus nidulans FGSC A4] | 74% | XP_659107 |
| Probable 4-hydroxy-2-oxoglutarate aldolase, mitochondrial | 74% | Q5BD77 |
| Hypothetical protein AN1503.2 [Aspergillus nidulans FGSC A4] | 74% | EAA63816 |
| Dihydrodipicolinate synthase-like protein AN1503 (DHDPS-like protein)[Aspergillus nidulans FGSC A4] | 74% | CBF84998 |
| Probable 4-hydroxy-2-oxoglutarate aldolase, mitochondrial [Aspergillus lentulus] | 76% | GAQ11949 |
| Dihydrodipicolinate synthetase family protein [Aspergillus ruber CBS 135680] | 71% | EYE96024 |
| 4-hydroxy-2-oxoglutarate aldolase [Rasamsonia emersonii CBS 393.64] | 70% | XP_013330421 |
| 4-hydroxy-2-oxoglutarate aldolase [Rasamsonia emersonii CBS 393.64] | 70% | KKA23809 |
| Dihydrodipicolinate synthetase family protein [Aspergillus fischeri NRRL 181] | 75% | XP_001262053 |
| Dihydrodipicolinate synthetase family protein [Aspergillus fischeri NRRL 181] | 75% | EAW20156 |
| Dihydrodipicolinate synthetase family protein [Aspergillus fumigatus Af293] | 76% | XP_747309 |
| Dihydrodipicolinate synthetase family protein [Aspergillus fumigatus Af293] | 76% | EAL85271 |
| Dihydrodipicolinate synthetase family protein [Aspergillus fumigatus A1163] | 76% | EDP48804 |
| Dihydrodipicolinate synthetase [Aspergillus fumigatus var. RP-2014] | 76% | KEY78362 |
| Hypothetical protein ASPGLDRAFT_42370 [Aspergillus glaucus CBS 516.65] | 70% | OJJ88774 |
| Dihydrodipicolinate synthetase family protein [Aspergillus fumigatus Z5] | 75% | KMK56661 |
| Dihydrodipicolinate synthase-like protein [Byssochlamys spectabilis No. 5] | 68% | GAD94194 |
| Hypothetical protein ASPVEDRAFT_125872 [Aspergillus versicolor CBS 583.65] | 73% | OJI97841 |
| Hypothetical protein ASPSYDRAFT_143055 [Aspergillus sydowii CBS 593.65] | 73% | OJJ63118 |
| Dihydrodipicolinate synthetase family protein [Aspergillus parasiticus SU-1] | 75% | KJK62017 |
| Dihydrodipicolinate synthase-like protein [Aspergillus oryzae RIB40] | 75% | XP_001817680 |
| dihydrodipicolinate synthetase family protein [Aspergillus flavus NRRL3357] | 75% | XP_002372806 |
| unnamed protein product [Aspergillus oryzae RIB40] | 75% | BAE55678 |
| dihydrodipicolinate synthetase family protein [Aspergillus flavus NRRL3357] | 75% | EED57194 |
| dihydrodipicolinate synthase/N-acetylneuraminate lyase [Aspergillus oryzae 3.042] | 75% | EIT74147 |
| dihydrodipicolinate [Aspergillus oryzae 100-8] | 75% | KDE76740 |
| dihydrodipicolinate synthetase [Aspergillus oryzae] | 75% | OOO13100 |
| Hypothetical protein PENDEC_c013GO6529 [Penicillium decumbens] | 68% | OQD73952 |
| Dihydrodipicolinate synthetase family protein [Aspergillus flavus AF70] | 75% | KJJ31403 |
| dihydrodipicolinate synthase-like protein [Aspergillus bombycis] | 74% | OGM50862 |
| Dihydrodipicolinate synthase-like protein [Aspergillus nomius NRRL 13137] | 75% | XP_015403196 |

TABLE 5-continued

BLAST Results obtained 07-19-2017 using sequence EHA21505.

| Annotation | Identity | Accession |
|---|---|---|
| Dihydrodipicolinate synthase-like protein [*Aspergillus nomius* NRRL 13137] | 75% | KNG82273 |
| Aldolase-type TIM barrel [*Penicillium griseofulvum*] | 70% | KXG52230 |
| Putative Dihydrodipicolinate synthetase family protein [*Penicillium brasilianum*] | 69% | CEJ57806 |
| Putative 4-hydroxy-2-oxoglutarate aldolase, mitochondrial [*Penicillium brasilianum*] | 69% | OOQ89866 |
| Aldolase-type TIM barrel [*Penicillium camemberti*] | 70% | CRL20929 |
| Hypothetical protein PENSOL_c027G11035 [*Penicillium solitum*] | 70% | OQD94259 |
| hypothetical protein PENNAL_c0010G10993 [*Penicillium nalgiovense*] | 70% | OQE91236 |
| Hypothetical protein ASPZODRAFT_133064 [*Penicilliopsis zonata* CBS 506.65] | 69% | OJJ46083 |
| hypothetical protein ACN42_g11115 [*Penicillium freii*] | 69% | KUM56111 |
| Aldolase-type TIM barrel [*Penicillium italicum*] | 69% | KGO71495 |

Example 10

To improve KDG formation in *A. niger*, a gluconate dehydratase activity may need to be enhanced. This can be accomplished by expressing a heterologous gluconate dehydratase in *A. niger*, or by enhancing the expression of an endogenous (native) gluconate dehydratase already present in the *Aspergillus* strain. However, endogenous gluconate dehydratases in filamentous fungi have not been identified. Nevertheless, the existence of such an enzymatic activity is essential for the Nonphosphorylated gluconate degradative pathway present in *A. niger* and many other microorganisms. So far, only a few gluconate dehydratases have been characterized in bacteria and archaea; and it has been found that they belong to the ILVD/EDD protein family (COG0129). This family includes dihydroxy acid dehydratases (DHADs) which are involved in short-chain amino acid biosynthesis, and catalyse the dehydration of 2,3-dihydroxy-3-methylbutanoate. DHADs are commonly named IlvD in bacteria or ILV-3 in fungi. COG0129 also contains sugar acid dehydratases, which are involved in the metabolism of hexose and pentose sugars, and include D-xylonate dehydratases, L-arabinonate dehydratase, D-gluconate dehydratases and 6-phosphogluconate dehydratases (EDD).

One way to predict the function of a gene in a particular genome, is to look for homologs of a gene for which the activity has been demonstrated in a close relative. For example, to predict gene functions in *Aspergillus*, very often the known genes from *Saccharomyces*, *Neurospora* or *Penicillium* are utilized for such a purpose. In this sense, Oliver et al., (2012) characterized the DHADs from *Aspergillus fumigatus* and found that this fungus, has 4 homologs (AfIlv3A, AfIlv3B, AfIlv3C and AfIlv3D) of the *Saccharomyces cerevisiae* ILV-3 for which, its function as a DHAD has been clearly demonstrated. Using gene deletions, Oliver et al., found that AfIlv3A was the real DHAD in *A. fumigatus*. No function for AfIlv3B, AfIlv3C and AfIlv3D was predicted by Oliver et al. Importantly, this publication also showed that *Aspergillus nidulans* had also four ILV-3 homologs, while *Aspergillus niger* had seven homologs (Anig1-7). Based on this report and others, it is proposed that the *A. niger* Anig5 (XP_001397198), Anig6 (XP_001392062) and Anig7 (XP_001394885) are good candidates to be sugar acid dehydratases. In particular, Anig5 which has 60% identity, 74% similarity to the *Achromobacter xylosoxidans* D-gluconate dehydratase gnaD (Kim & Lee. 2008). Due to the reannotation and renaming of genes in GenBank, other annotation/names for Anig5, Anig6 and Anig7 are given in the table below. One skilled in the art may determine that the names used to annotate the genome of the *A. niger* strain CBS 513.88 may be different in other *A. niger* strains.

TABLE 6

Annotations in *A. niger*

| Annotations in *A.niger* CBS513.88, accordingly Oliver et al., 2012 | Other Annotations |
|---|---|
| Anig5 | XP_001397198; ANI_1_908134; NT_166530; Gene ID 4988271. |
| Anig6 | XP_001392062; ANI_1_2174064; NT_166523; Gene ID 4982256. |
| Anig7 | XP_001394885: ANI_1_2454094; NT_166526; Gene ID 4985143. |

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

All references cited herein, including those below and including but not limited to all patents, patent applications, and non-patent literature referenced below or in other portions of the specification, are hereby incorporated by reference herein in their entirety.

Allam A M, et al., (1975). Formation and cleavage of 2-keto-3-deoxygluconate by 2-keto-3-deoxygluconate aldolase of *Aspergillus niger*. J. Bacteriol. 124:1128-1131.

Conway, T. (1992). The Entner-Doudoroff pathway: history, physiology and molecular biology. FEMS Microbiol. Rev 9: 1-27.

Elzainy T A. et al., (1973). New pathway for nonphosphorylated degradation of gluconate by *Aspergillus niger*. J. Bacteriol. 114: 457-459.

Flipphi et al., (2009). Biodiversity and evolution of primary carbon metabolism in *Aspergillus nidulans* and other *Aspergillus* spp. Fungal Genet Biol. 46: S19-S44.

Hilditch S., et al. (2007). The missing link in the fungal D-galacturonate pathway. Identification of the L-threo-3-deoxy-hexulosonate aldolase. J. Biol. Chem. 282: 26195-26201.

Hobbs J K., et al. (2016). KdgF, the missing link in the microbial metabolism of uronate sugars from pectin and alginate. PNAS. 113: 6188-6193.

Kim S., Lee S B. (2005). Identification and characterization of *Sulfolobus solfataricus* D-gluconate dehydratase: a key enzyme in the non-phosphorylated Entner-Duodoroff pathway. Biochem. J. 387: 271-280.

Kim S., Lee S B. (2006). Catalytic promiscuity in dihydroxy-acid dehydratase from the thermoacidophilic archeon *Sulfolobus solfataricus*. J. Biochem. 139: 591-596.

Kim S. and Lee, S. B. (2008) Identification and Characterization of the Bacterial D-Gluconate Dehydratase in *Achromobacter xylosoxidans*. Biotechnol. Bioprocess Eng. 13: 436-444.

Martens-Uzunova, E. and Shcaap, P J. (2008). An evolutionary conserved D-galacturonic acid metabolic pathway operates across filamentous fungi capable of pectin degradation. Fungal Genet. Biol. 45: 1449-1457.

Matsubara K. et al. (2014). One-Step Synthesis of 2-Keto-3-Deoxy-D-Gluconate by Biocatalytic Dehydration of D-Gluconate. J. Biotechnol 191: 69-77.

Müller H M. (1985). Utilization of Gluconate by *Aspergillus niger*. I. Enzymes of Phosphorylating and Nonphosphorylating Pathways. Zentralbl Mikrobiol. 140: 475-484.

Müller H M. (1986). Utilization of Gluconate by *Aspergillus niger*. II. Enzymes of Degradation Pathways and Main End Products. Zentralbl Mikrobiol. 141: 461-469.

Oliver J. D., et al., (2012). The *Aspergillus fumigatus* Dihydroxyacid Dehydratase Ilv3/IlvC is required for full virulence. PLOS One. Vol 7, issue 9. e43559

Pel, H., et al. (2007). Genome sequence and analysis of the versatile factory *Aspergillus niger* CBS 513.88 Nat. Biotechnol. 25: 221-231.

Pouyssegur J. (1973). Preparation microbiologique du 2-ceto-3-desoxy-D-gluconate 1-$^{14}$C ou U-$^{14}$C. J. Labell. Compounds 9: 3-13.

Suvorova I A., (2011) Comparative Genomic Analysis of the Hexuronate Metabolism Genes and Their Regulation in Gammaproteobacteria. J. Bacteriol. 193: 3956-3963.

van Dijken J. et al., (2002). Novel pathway for alcoholic fermentation of y-gluconolactone in the yeast *Saccharomyces bulderi*. J. Bacteriol. 184: 672-678.

Wiebe M G. et al., (2010). Bioconversion of D-gacturonate to keto-deoxy-L-galactonate (3-deoxy-L-threo-hex-2-ulosonate) using filamentous fungi. BMC Biotechnology, 10:63.

U.S. Pat. No. 7,125,704.
U.S. Pat. No. 7,510,861.
U.S. Pat. No. 8,383,375.
U.S. Pat. No. 7,858,775.

---

What is claimed is:

1. A genetically modified filamentous fungus having reduced 2-Keto-3-Deoxy-Gluconate (KDG) aldolase enzyme activity as compared to the KDG aldolase enzyme activity in a wild type counterpart of said filamentous fungus, wherein said filamentous fungus is an *Aspergillus niger* strain.

2. The filamentous fungus claim of 1, wherein the *Aspergillus niger* strain is selected from the group consisting of NRRL 322, NRRL 328, NRRL 566, NRRL 599 and NRRL 2270.

3. The filamentous fungus of claim 1, wherein the genetic modification results in reduced endogenous KDG aldolase enzyme activity.

4. The filamentous fungus of claim 1, wherein the genetic modification is a mutation.

5. The filamentous fungus of claim 4, wherein the mutation is selected from the group consisting of a frame shift mutation, a substitution mutation, an insertion mutation, a loss of function mutation, a gain of function mutation, an inactivation mutation, a translocation mutation and a deletion mutation.

6. The filamentous fungus of claim 4, wherein the mutation is in the promotor region, the 3' untranslated region, the 5' untranslated region and/or a regulatory sequence of a 2-Keto-3-Deoxy-Gluconate (KDG) aldolase gene.

7. The filamentous fungus of claim 4, wherein the mutation is in a nucleic acid sequence encoding a polypeptide having complete sequence identity to SEQ ID NO:1.

8. The filamentous fungus of claim 4, wherein the mutation is a deletion of a gene having the nucleic acid sequence of SEQ ID NO:2.

9. The filamentous fungus of claim 4, wherein the mutation is in a nucleic acid sequence encoding a KDG aldolase enzyme comprising the amino acid sequence of SEQ ID NO:1.

10. The filamentous fungus of claim 4, wherein the mutation inhibits expression of the polypeptide comprising SEQ ID NO:1.

11. The filamentous fungus of claim 1, wherein the enzyme having reduced 2-Keto-3-Deoxy-Gluconate (KDG) aldolase enzyme activity has the classification of EC4.1.2.51.

12. A method of producing 2-Keto-3-Deoxy-Gluconate (KDG) or a furan derivative comprising:
culturing the genetically modified filamentous fungus of claim 1 in a culture medium, wherein the level of KDG or a furan derivative accumulated by the genetically modified filamentous fungus is higher than the level of KDG or a furan derivative accumulated by a wild type counterpart of said filamentous fungus, thereby producing KDG or a furan derivative.

13. The method of claim 12, wherein the genetically modified filamentous fungus has been transformed with a nucleic acid sequence that inactivates a gene encoding a KDG aldolase enzyme, reduces expression of a gene encoding a KDG aldolase enzyme or inhibits expression of a gene encoding a KDG aldolase enzyme.

14. A method of decreasing D-glyceraldehyde production from 2-Keto-3-Deoxy-Gluconate in a filamentous fungus comprising:
culturing the genetically modified filamentous fungus of claim 1 in a culture medium, wherein the level of D-glyceraldehyde production from 2-Keto-3-Deoxy-Gluconate in the genetically modified filamentous fungus is decreased from the level of glyceraldehyde production from 2-Keto-3-Deoxy-Gluconate in a wild type counterpart of said filamentous fungus, thereby decreasing D-glyceraldehyde from 2-Keto-3-Deoxy-Gluconate.

15. The method of claim 14, wherein the genetically modified filamentous fungus has been transformed with a nucleic acid sequence that inactivates a gene encoding a KDG aldolase enzyme, reduces expression of a gene encoding a KDG aldolase enzyme or inhibits expression of a gene encoding a KDG aldolase enzyme.

* * * * *

UNITED STATES PATENT AND TRADEMARK OFFICE
CERTIFICATE OF CORRECTION

| | | |
|---|---|---|
| PATENT NO. | : 11,708,571 B2 | Page 1 of 1 |
| APPLICATION NO. | : 17/056146 | |
| DATED | : July 25, 2023 | |
| INVENTOR(S) | : Krebs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 46 days.

Signed and Sealed this
Sixth Day of August, 2024

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 312
<212> TYPE: PRT
<213> ORGANISM: Unknown
<220> FEATURE:
<223> OTHER INFORMATION: Uncharacterized protein OS=Aspergillus niger

<400> SEQUENCE: 1

Met Ala Ile Thr Pro Arg Pro Leu Lys Pro Gly Ile Tyr Val Pro Thr
1               5                   10                  15

Val Ala Phe Phe Thr Ser Pro Asn Glu Asp Leu Asp Leu Ser Thr Thr
            20                  25                  30

Ala Leu His Ala Thr Tyr Leu Ala Gln Ala Gly Val Thr Gly Leu Val
        35                  40                  45

Val Gln Gly Ser Asn Gly Glu Ala Val His Leu Ser Arg Glu Glu Arg
    50                  55                  60

Asn Leu Ile Thr Ser Thr Thr Arg Arg Ala Leu Asp Ser His Ala Pro
65                  70                  75                  80

Ser Ala Pro Leu Ile Val Gly Cys Gly Ala Ala Ser Thr Arg Glu Thr
                85                  90                  95

Ile Gln Leu Cys Gln Asp Ala Ala Ala Ser Gly Gly Asp Tyr Thr Leu
            100                 105                 110

Ile Leu Pro Pro Ser Tyr Tyr Lys Ser Leu Leu Ser Pro Lys Asp Leu
        115                 120                 125

Leu Asp His Phe Arg Leu Val Ala Ser Ala Ser Pro Ile Pro Ile Leu
    130                 135                 140

Val Tyr Asn Phe Pro Gly Ala Ser Ser Gly Leu Asp Leu Ser Ser Asp
145                 150                 155                 160
```

```
Asp Ile Leu Ala Leu Ala Glu His Pro Asn Ile Val Gly Val Lys Leu
            165                 170                 175

Thr Cys Gly Asn Thr Gly Lys Leu Ala Arg Ile Ala Ala Ala Ala Glu
        180                 185                 190

Pro Gly Phe Met Thr Phe Gly Gly Ser Ala Asp Phe Thr Leu Gln Thr
    195                 200                 205

Leu Val Ala Gly Gly His Gly Val Ile Gly Gly Val Ala Asn Leu Ile
210                 215                 220

Pro Arg Leu Ser Val Arg Val Met Glu Leu Tyr Gln Ala Gly Gln Val
225                 230                 235                 240

Glu Glu Ala Gln Arg Leu Gln Ala Ile Val Ala Arg Ala Asp Trp Gln
            245                 250                 255

Ala Ile Lys Gly Gly Phe Val Ala Val Lys Ser Ala Leu Gln Thr Tyr
        260                 265                 270

Arg Gly Tyr Gly Ala Leu Pro Arg Pro Cys Val Val Pro Ser Glu
    275                 280                 285

Ala Gln Ala Thr Ala Trp Lys Asp Ser Phe Ala Glu Ala Met Glu Leu
    290                 295                 300

Glu Arg Gln Leu Glu Lys Gln Ala
305                 310
```

<210> SEQ ID NO 2
<211> LENGTH: 939
<212> TYPE: DNA
<213> ORGANISM: Artificial Sequence
<220> FEATURE:
<223> OTHER INFORMATION: Synthetic

<400> SEQUENCE: 2

```
atggccatta caccccgccc cctcaaaccc ggcatctacg tcccaaccgt cgccttcttc      60
acctctccca cgaagacct cgacctctcc accaccgccc tccacgccac ctacctcgct     120
caagccggcg tcaccggtct agtcgtgcaa ggcagcaacg tgaagccgt ccacctcagc     180
cgcgaagagc gcaacctcat cacttccacc accgtcgcg ctctcgactc tcacgccccc     240
tccgccccgc tcatcgtcgg ctgcggcgcc gcctccaccc gcgagaccat ccagctgtgc     300
caagacgccg ccgcctccgg aggcgactat accctgatcc tccctccctc ctactacaaa     360
tccctcctct ctcccaagga ccttcttgat cacttccgcc tgtcgcctc cgcctccccc     420
atccccatcc tggtgtacaa cttccccggc gcctcttcgg gcctggacct ctcctccgac     480
gacatcctcg ccttggcgga gcaccccaac atcgtcggcg tgaagctgac ctgtggaaac     540
acgggtaaac tggcgcgcat tgccgccgcc gcgaacccg gtttcatgac ctttggtggt     600
tccgctgatt tcactctcca gacgctggtg gcaggcggtc atggagtgat tggcggcgtg     660
gcgaacctga tccctcgttt gagtgtgcgc gtgatggagc tgtatcaggc gggacaggtc     720
gaagaggccc agcggttgca ggccattgta gcgcgtgcgg actggcaggc tatcaagggt     780
ggttttgtag cggtgaagag tgcgttgcag acgtaccgcg gatacggagc attgccgaga     840
cggccgtgtg tggtgccgtc agaggcgcag gcgacggcgt ggaaggattc ttttgcggag     900
gctatggagc tggagagaca gttagagaag caggcctag                           939
```

<210> SEQ ID NO 3
<211> LENGTH: 939
<212> TYPE: DNA
<213> ORGANISM: Artificial Sequence
<220> FEATURE:
<223> OTHER INFORMATION: Synthetic

<400> SEQUENCE: 3

```
atggcaatta cccctcgccc gctgaagccg ggcatttacg tgccgaccgt tgccttttc    60
accagcccga atgaggacct ggacctgagc accaccgcac tgcatgcaac ctatctggca   120
caggcaggtg tgaccggcct ggttgtgcag ggtagcaatg tgaagccgt gcatctgagc    180
cgtgaggagc gtaacctgat tacaagcacc acccgccgtg cactggatag ccatgccccg   240
agtgccccgc tgatcgttgg ttgcggtgca gcaagcaccc gcgaaaccat tcagctgtgt   300
caagatgcag ccgccagtgg cggcgactat actctgatcc tgccgccgag ctactacaaa   360
agcctgctga gtccgaagga tctgctggac catttcgcc tggttgccag cgcaagcccg    420
attccgattc tggtgtataa ctttccgggc gccagtagcg gtctggacct gagtagcgat   480
gatattctgg cactggcaga gcatccgaac attgtgggcg tgaaactgac ctgcggtaac   540
acaggcaaac tggcacgtat cgcagccgca gcagaaccgg gttttatgac ctttggcggt   600
agtgccgact ttaccttaca gaccctggtt gccggtggtc atggtgtgat tggcggcgtg   660
gcaaatctga ttccgcgcct gagcgttcgt gttatggagc tgtaccaggc aggtcaggtg   720
gaagaagccc agcgtctgca ggccattgtg gcacgtgccg actggcaggc cattaaaggc   780
ggttttgtgg ccgtgaaaag cgccctgcag acctaccgcg ttatggtgc actgccgcgt    840
cgtccgtgtg tggtgcctag cgaagcacag gccaccgcat ggaaagatag ctttgccgag   900
gctatggaac tggaacgcca gctggaaaaa caagcctaa                          939
```

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4

```
cttgatatcg aattcgacga ggtgggatta ttgctg                              36
```

<210> SEQ ID NO 5
<211> LENGTH: 35
<212> TYPE: DNA
<213> ORGANISM: Artificial Sequence
<220> FEATURE:
<223> OTHER INFORMATION: Synthetic

<400> SEQUENCE: 5

```
catcgtttgc atcatcaggg gatggggaga atgcg                               35
```

<210> SEQ ID NO 6
<211> LENGTH: 38
<212> TYPE: DNA
<213> ORGANISM: Artificial Sequence
<220> FEATURE:
<223> OTHER INFORMATION: Synthetic

<400> SEQUENCE: 6

```
cacggctcag actctcccac atcttctaca tacccatc                            38
```

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7

```
ctagtggatc ccccgggcgc ctcatattcc tcgatgc                                37
```

<210> SEQ ID NO 8
<211> LENGTH: 8040
<212> TYPE: DNA
<213> ORGANISM: Artificial Sequence
<220> FEATURE:
<223> OTHER INFORMATION: Synthetic

<400> SEQUENCE: 8

```
ctaaattgta agcgttaata ttttgttaaa attcgcgtta aatttttgtt aaatcagctc        60
attttttaac caataggccg aaatcggcaa atcccttat aaatcaaaag aatagaccga       120
gataggttg agtgttgttc cagtttggaa caagagtcca ctattaaaga acgtggactc       180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg aagggcgat cggtgcgggc ctcttcgcta ttacgccagc tggcgaaagg     540
gggatgtgct gcaaggcgat taagttgggt aacgccaggt ttttcccagt cacgacgttg     600
taaaacgacg gccagtgagc gcgcgtaata cgactcacta gggcgaat tgggtaccgg       660
gcccccctc gaggtcgacg gtatcgataa gcttgatatc gaattcgacg aggtgggatt      720
attgctggcc agcgggcggc gcgtcgaggt ccgccggcgc aggggatgat gagacgagag     780
tttgtagggc gtggcagctg aggaggacga gttctccgtc gtggtggtgt ccagcagatc     840
gggggagctt ttgcgacggc gcgatgacga gtgagtctgg agacgagctc gctttgcagg     900
aggctcggag tccggctggt cggggaatg gccgtgatga ggatctcgtc gcagggagac     960
acggacaggc atcagggtgg tggaggtcat tcgggaggat cgaggagggg agaggaattg    1020
agacgtgggg ggaaagaaag gtcaggaggg atgcgtgcac ggcatgtcag ggccagtcgg    1080
gggcaattcg gaggattgaa gttggcagga ggttttttgg gcgaagctga agcactcgag    1140
aatcgcagct gcaggtctgg atgtgttccg gattgggagg agttgaaagt tgtatctta    1200
cggataccgc agcaggtatg tctcagtacc tgacaggaca ggtgttaccg ccaggatgta    1260
tgatacctgt cacaacgata cctcactgga ctagcttaac atacatacat acatcataca    1320
tcttcacatc ttcactcttc ttctactgca tcaacttctg cgtgaagcac ttctaattca    1380
tccaccccat tcactccttt tccggctcac ctcatttctc cgaggaacca attctccgac    1440
gactacccca ttcctctacc ataatgcttc ccagcacgac gtggggtgg gagctcccct    1500
gacttgccat aggaggggat ctgctggaga gagtgtgggg tgcgtggggg tttggctgga    1560
ttgttttctg ctcgacgctg tctggatgga gtcaaccggc tcaatgtccg actctctccc    1620
aacttaactg gaactgtttc ccctcttagc cacccactgg cttgctttct tatatatcat    1680
ggcaacgact tcctcgttgc tttccatctg tcctcctctt cttcctcctc ctccttcctc    1740
ttcccccgca ttctccccat cccctgatga tgcaaacgat gagctggtat atgacactgg    1800
aatgcatgca gtcatggata cgattcagtg ggtgccgggc caaaagcggg gcattccgga    1860
tgcgacgatc acctgaccca tctccagccg ctagcgatgg cctaaggcca cttcccgagg    1920
ccgcgccgtc gagataacag ctggagagga tccccttccc ccatcctcca tcctccgata    1980
```

```
aggaatgccc ccaactcaca cgtcatcgcc gttgctgccg ccgcaaggcc agttgtcgca   2040
ttccctctct gatcatcacc ccccagttta cctggtgaga tgatacgaat tatcaatgag   2100
aaggcaaaca atatatagac agcagaaact ccgagtttca acgggttcta tttcaggaac   2160
acggctgcgg tctggattgg gtcgggctga gataccgact ggtggcgtca gtggcgggta   2220
cggacggagt cgtcctgtcc gctcgtagac gcttcccccg gactgatatc aggccccggc   2280
aaccaactgg cttcgattcc cctcccatgg cagcagcagt gcctaccaca tgggatcagg   2340
cttttgcctg ttgttctaag ttttgcagac agaattttcg tatgcgttac cactcttttt   2400
ctttcagcga ccattcccgt tgtagttgta aacccaataa taggtggctg ccgtgggagc   2460
ctgagtcaac ccaaccagaa cctttctagt agattctccc tcccaagcgc ttcagcaacg   2520
aagcgtattg gagaaccaaa tgacgcagac caggcggatt ccggcgcaat agccggatgg   2580
caagggaatc ccccaggagg tgccagaagc gtcgcccgaa aggtacttcg tctgacaggc   2640
taacaccgct cggggccaagg tccctgctgc tcttttccct ttattgcgac ttgacctcta   2700
agccattccc ttgcatcacg ttatctcact gaccgatcct ctgactaagg cgcttcgcct   2760
ccgcctcccc tcattcacct cctctcctga ctacttaagc cttctcttcc ttccttcctc   2820
taccaaccct ccttcatccc tcatacctct catcctacca ctcaccttcc gcgcatcgcc   2880
atctgcgatt ctctccacaa caactccacc taatcacata caccattaac tgcgcttcta   2940
caacatgaaa aagcctgaac tcaccgcgac gtctgtcgag aagtttctga tcgaaaagtt   3000
cgacagcgtc tccgacctga tgcagctctc ggagggcgaa gaatctcgtg ctttcagctt   3060
cgatgtagga gggcgtggat atgtcctgcg ggtaaatagc tgcgccgatg gtttctacaa   3120
agatcgttat gtttatcggc actttgcatc ggccgcgctc ccgattccgg aagtgcttga   3180 cattgggaa ttcagcgaaa gcctgaccta ttgcatctcc cgccgtgcac agggtgtcac   3240
gttgcaagac ctgcctgaaa ccgaactgcc cgctgttctg cagccggtcg cggaggccat   3300
ggatgcgatc gctgcggccg atcttagcca gacgagcggg ttcggcccat tcggaccgca   3360
aggaatcggt caatacacta catggcgtga tttcatatgc gcgattgctg atccccatgt   3420
gtatcactgg caaactgtga tggacgacac cgtcagtgct tccgtcgcgc aggctctcga   3480
tgagctgatg ctttgggccg aggactgccc cgaagtccgg cacctcgtgc acgcggattt   3540
cggctccaac aatgtcctga cggacaatgg ccgcataaca gcggtcattg actggagcga   3600
ggcgatgttc ggggattccc aatacgaggt cgccaacatc ttcttctgga ggccgtggtt   3660
ggcttgtatg gagcagcaga cgcgctactt cgagcggagg catccggagc ttgcaggatc   3720
gccgcggctc cgggcgtaca tgctccgcat tggtcttgac caactctatc agagcttggt   3780
tgacggcaat ttcgatgatg cagcttgggc gcagggtcga tgcgacgcaa tcgtccgatc   3840
cggagccggg actgtcgggc gtacacaaat cgcccgcaga agcgcggccg tctggaccga   3900
tggctgtgta gaagtactcg ccgatagtgg aaaccgacgc cccagcactc gtccgagggc   3960
aaaggaatag tgccttattt tgatctttct tctttagcac ggctcatcta cggttgagtg   4020
gcctgcatgg cgttgggacg gttgtttat cggttttatg acacggataa attgggcata   4080
ccttagggtc accatcttct atggtgcctt gcgacattct ttcacctagg aatcaatcca   4140
ataattatat tccacctgat atcttgcttg cactgttttcc tgtagattta gtaggaccgc   4200
ccgaagtaga ccgccacgct agcatagacg tggtccacat gcaattcagg acggcgtcca   4260 ccccccttaca gatcgtatgc gaagaaatta actagataat aaaatggctt catcttcatc   4320
```

-continued

```
ttcatctacc tatacaatcg ctaacaagga actaatagac atcgcaggtg agtcaccgtc    4380
ttcaccaccc gtatcttagc acgtgactat accgtcccaa ggcggcgtgg gacaggaaag    4440
tagcttccat tcatgaactc gacctgagag agcagttgca gacgtgtaac acgctggaga    4500
tgtgagcatc agtcgtgatg ccctcctact tctaccacat tgcgatcgaa ttatttgctc    4560
gcccgcactc tgacctccat ggcacctacc caggcgtgga caagcactcg acatcgctat    4620
ccttcgactc cgcatgcgaa gctctacccc cgttccagaa gcgccccga cactcaccgt     4680
gggcacatcg atcctctcgt catcaagcgc atgggaaaca cccacgcccc tcatccaaca    4740
ctttcgccga aacccacggc tcagactctc ccacatcttc tacatacccca tcatcatcat   4800
catcatctat acaaacggca acaccaaata cgaatcaaac tccaccccac aatgaacctc    4860
atgcacctgc tctttctccc ccacatcccc tcccgatccc tccccttcca ccggaccaaa    4920
ctccacctcc ggataacaca aatcacgccc cgccaccctc aacataatcc cctccccagc    4980
accaaacacc attcccatcg gccacaacgt aatatcaatc ggcacgatct ttcccgccgg    5040
gatgctctcc gcccgatcat gtctatacac aatctcatgc tctgtcgaga gcgtctcgtc    5100
ccgtgtgacg gcgtgcgacg cacgcaggaa ccctgcggt ccgagcgtct tggctgtgtt     5160
gacgttgggg acggcgtcaa cgggcacggg acacgggtag ttgaggtgtt cgagaagcgt    5220
gccggtggcg gagatcttgc ggatttgcac gatgatgtcc atgtctgtgt ggtgggggt     5280
ggagagccac agatgtacgc gggggtaccc ggctaactga gtggggtgg ggaagtggag     5340
ggtgaagtcc tattatttgt taggagatat tgagagagag ggtatgttaa gggggagacg    5400
tacggaggtg ccatggaggg cggaatgggt tgttgaggtg actgtgcttg ggagagaggg    5460
ttggagggtc ttggttgatg cgttgaggta gaatttcttg agctcctgcc gggttaatgg    5520
gtaggtatgt tcgggcgtt cgaggatggt tggcacagag ctgccttcga atccaaggag     5580
ggagaggcgc accggtggtg tgctttccca gtcgttgggt gtgttcttaa gatagcggtc    5640
gaagaaacga gagaggtcgt cgaccatctc gggtcggtat agatcgtacc attcttggta    5700
tgggtgcacg cggagccatt tcgggtgct ctgggcggtg cggaaggttt cgaaggagcc     5760
gcgcgtgtgc agcatcgagg aatatgaggc gcccggggga tccactagtt ctagagcggc    5820
cgccaccgcg gtggagctcc agcttttgtt ccctttagtg agggttaatt gcgcgcttgg    5880
cgtaatcatg gtcatagctg tttcctgtgt gaaattgtta tccgctcaca attccacaca    5940
acatacgagc cggaagcata agtgtaaag cctggggtgc ctaatgagtg agctaactca     6000
cattaattgc gttgcgctca ctgcccgctt tccagtcggg aaacctgtcg tgccagctgc    6060
attaatgaat cggccaacgc gcggggagag gcggtttgcg tattgggcgc tcttccgctt    6120
cctcgctcac tgactcgctg cgctcggtcg ttcggctgcg cgagcggta tcagctcact     6180
caaaggcggt aatacggtta tccacagaat caggggataa cgcaggaaag aacatgtgag    6240
caaaaggcca gcaaaaggcc aggaaccgta aaaaggccgc gttgctggcg tttttccata    6300
ggctccgccc cctgacgag catcacaaaa atcgacgctc aagtcagagg tggcgaaacc     6360
cgacaggact ataaagatac caggcgtttc ccctggaag ctccctcgtg cgctctcctg     6420
ttccgaccct gccgcttacc ggatacctgt ccgcctttct cccttcggga agcgtggcgc    6480
tttctcatag ctcacgctgt aggtatctca gttcggtgta ggtcgttcgc tccaagctgg    6540
gctgtgtgca cgaaccccc gttcagccg accgctgcgc cttatccggt aactatcgtc      6600
ttgagtccaa cccggtaaga cacgacttat cgccactggc agcagccact ggtaacagga    6660
ttagcagagc gaggtatgta ggcggtgcta cagagttctt gaagtggtgg cctaactacg    6720
```

```
gctacactag aaggacagta tttggtatct gcgctctgct gaagccagtt accttcggaa    6780
aaagagttgg tagctcttga tccggcaaac aaaccaccgc tggtagcggt ggtttttttg    6840
tttgcaagca gcagattacg cgcagaaaaa aaggatctca agaagatcct ttgatctttt    6900 ctacgggtc tgacgctcag tggaacgaaa actcacgtta agggattttg gtcatgagat     6960
tatcaaaaag gatcttcacc tagatccttt aaattaaaa atgaagtttt aaatcaatct     7020
aaagtatata tgagtaaact tggtctgaca gttaccaatg cttaatcagt gaggcaccta    7080
tctcagcgat ctgtctattt cgttcatcca tagttgcctg actccccgtc gtgtagataa    7140
ctacgatacg ggagggctta ccatctggcc ccagtgctgc aatgataccg cgagacccac    7200
gctcaccggc tccagattta tcagcaataa accagccagc cggaagggcc gagcgcagaa    7260
gtggtcctgc aactttatcc gcctccatcc agtctattaa ttgttgccgg gaagctagag    7320
taagtagttc gccagttaat agtttgcgca acgttgttgc cattgctaca ggcatcgtgg    7380
tgtcacgctc gtcgtttggt atggcttcat tcagctccgg ttcccaacga tcaaggcgag    7440
ttacatgatc ccccatgttg tgcaaaaaag cggttagctc cttcggtcct ccgatcgttg    7500
tcagaagtaa gttggccgca gtgttatcac tcatggttat ggcagcactg cataattctc    7560
ttactgtcat gccatccgta agatgctttt ctgtgactgg tgagtactca accaagtcat    7620
tctgagaata gtgtatgcgg cgaccgagtt gctcttgccc ggcgtcaata cgggataata    7680
ccgcgccaca tagcagaact ttaaaagtgc tcatcattgg aaaacgttct cggggcgaa     7740 aactctcaag gatcttaccg ctgttgagat ccagttcgat gtaacccact cgtgcaccca    7800
actgatcttc agcatctttt actttcacca gcgtttctgg gtgagcaaaa acaggaaggc    7860
aaaatgccgc aaaaaaggga ataagggcga cacggaaatg ttgaatactc atactcttcc    7920
tttttcaata ttattgaagc atttatcagg gttattgtct catgagcgga tacatatttg    7980
aatgtattta gaaaaataaa caaatagggg ttccgcgcac atttccccga aaagtgccac    8040
```

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tcgttgcttt ccatctgtcc                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gtggggtgga gtttgattcg                                                    20

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11

```
cgatcagaaa cttctcgaca gac                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
gatgtgatag tggggtgga atc                                               23
```